United States Patent
Pereira

(10) Patent No.: US 12,023,324 B2
(45) Date of Patent: *Jul. 2, 2024

(54) CONTROLLED RELEASE FORMULATIONS OF RILUZOLE AND THEIR USES

(71) Applicant: Icahn School of Medicine at Mount Sinai, New York, NY (US)

(72) Inventor: Ana Pereira, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 24 days.

This patent is subject to a terminal disclaimer.

(21) Appl. No.: 17/882,707

(22) Filed: Aug. 8, 2022

(65) Prior Publication Data

US 2023/0054455 A1    Feb. 23, 2023

Related U.S. Application Data

(63) Continuation of application No. 17/026,181, filed on Sep. 19, 2020, now Pat. No. 11,439,626.

(60) Provisional application No. 62/903,282, filed on Sep. 20, 2019.

(51) Int. Cl.
| | | |
|---|---|---|
| C07D 277/82 | (2006.01) | |
| A61K 31/428 | (2006.01) | |
| A61P 25/00 | (2006.01) | |

(52) U.S. Cl.
CPC .................. *A61K 31/428* (2013.01)

(58) Field of Classification Search
CPC ...... C07D 277/82; A61K 31/428; A61P 25/00
See application file for complete search history.

(56) References Cited

U.S. PATENT DOCUMENTS

| | | |
|---|---|---|
| 5,674,885 A | 10/1997 | Boireau et al. |
| 2007/0190043 A1 | 8/2007 | Sych et al. |
| 2014/0243344 A1 | 8/2014 | Cedarbaum et al. |
| 2017/0360762 A1 | 12/2017 | Matsuda et al. |

FOREIGN PATENT DOCUMENTS

| | | |
|---|---|---|
| CA | 2 849 213 | 1/2013 |
| EP | 3 235 498 | 10/2017 |

OTHER PUBLICATIONS

"International Preliminary Report of Patentability in PCT/US20/051682", Mar. 31, 2022, 5 pages.
"International Search Report and written Opinion in U.S. Application No. PCT/US2020/051682", Dec. 4, 2020, 11 Pages.
"Extended European Search Report in EP Application No. 20865757.7", Sep. 14, 2023, 11 pages.
Bruno Rene, et al., "Population 1-10 pharmacokinetics of riluzole in patients with amyotrophic lateral sclerosis", Clinical Pharmacology and Therapeutics, Technical Fields Searched (IPC) vol. 62, No. 5,, Nov. 1, 1997, pp. 518-526.
Endrenyi Laszlo, et al., "Metrics for the 1-10 Evaluation of Bioequivalence of Modified-Release Formulations", The AAPS Journal, Springer US, Boston, vol. 14, No. 4,, Aug. 22, 2012, pp. 813-819.
Yarosh M.M., et al., "Agricultural and Aquacultural uses of Waste Heat", Oak Ridge National Laboratory (ORNL), Jul. 1, 1972.
"Office Action in Canadian Application No. 3151459", Oct. 26, 2023, 3 pages.

*Primary Examiner* — Brenda L Coleman
(74) *Attorney, Agent, or Firm* — IP Spring

(57) ABSTRACT

Disclosed herein are controlled release compositions comprising riluzole and the uses thereof.

19 Claims, 25 Drawing Sheets

Fig. 11A
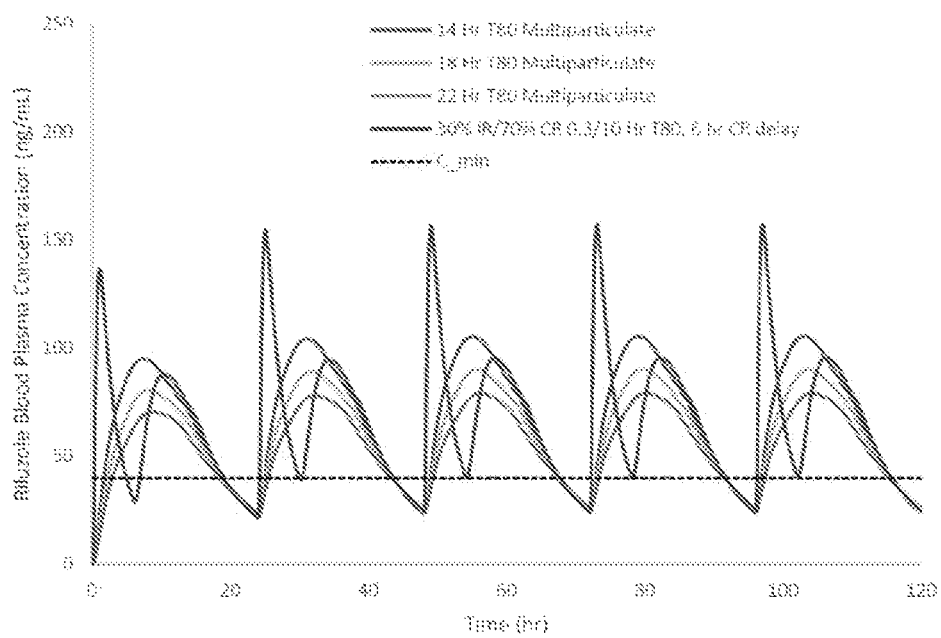
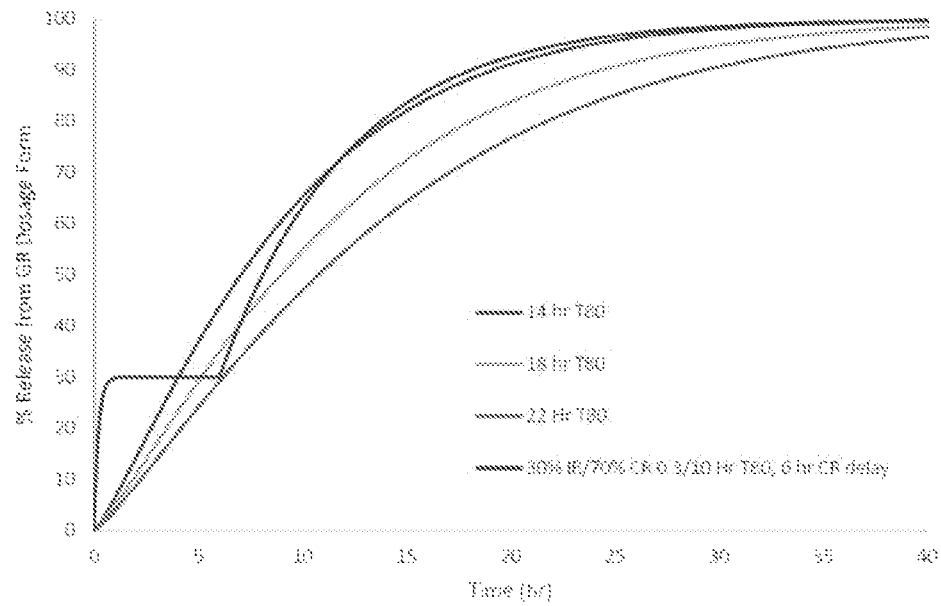
Fig. 11B

CONTROLLED RELEASE FORMULATIONS OF RILUZOLE AND THEIR USES

RELATED APPLICATION

This application is a continuation of U.S. application Ser. No. 17/026,181, entitled "Controlled Release Formulations of Riluzole and Their Uses" and filed on Sep. 19, 2020, which claims the benefit of U.S. Provisional Application No. 62/903,282, entitled "Controlled Release Formulations of Riluzole and Their Uses," and filed on Sep. 20, 2019, which is incorporated herein by reference in its entirety for all purposes.

BACKGROUND OF THE INVENTION

Riluzole is a member of the benzothiazole class. Chemically, riluzole is 2-amino-6-(trifluoromethoxy)benzothiazole (hereafter referred to as "riluzole") and is approved for treatment of amyotrophic lateral sclerosis (ALS). Riluzole is a white to slightly yellow powder that is very soluble in dimethylformamide, dimethylsulfoxide and methanol, freely soluble in dichloromethane, sparingly soluble in 0.1 N HCl and very slightly soluble in water and in 0.1 N NaOH. Riluzole is available as RILUTEK™, a capsule-shaped, white, film-coated tablet for oral administration containing 50 mg of riluzole and also as TIGLUTIK™, an oral suspension that is a slightly brown, opaque, homogeneous suspension containing 50 mg of riluzole per 10 mL of suspension. TIGLUTIK™ also contains the following inactive ingredients: magnesium aluminum silicate, noncrystallizing sorbitol solution, polyoxyl 20 cetostearyl ether, purified water, saccharin sodium, simethicone emulsion, sodium lauryl sulfate, and xanthan gum.

Riluzole is useful for treating central nervous system ("CNS") and/or depression/anxiety states, including neurological diseases. These include, but are not limited to, bipolar disorder, treatment resistant and major depression, obsessive-compulsive disorder, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease.

The use of riluzole is significantly constrained due to high levels of variability in hepatic metabolism of the drug, dose-dependent effects on the liver, and a negative food effect associated with the drug when administered with meals. In addition, riluzole has a very low solubility in water, poor oral palatability, and pH-dependent chemical stability. The approved US labeling for RILUTEK™ notes that riluzole tablets should be taken at least 1 hour before, or 2 hours after, a meal to avoid food-related decreases in bioavailability that may interfere with the ability to achieve or maintain therapeutic blood concentrations. Despite riluzole's approval over 20 years ago, these multiple clinical constraints of riluzole have persisted and limited the clinical application of riluzole. The controlled release (or modified release—"modified" and "controlled" are used interchangeably in this application) riluzole compositions described herein address these needs.

SUMMARY OF THE INVENTION

In one embodiment, the present invention relates to a pharmaceutical composition comprising about 100 mg to 125 mg of riluzole or a pharmaceutically acceptable derivative thereof, which provides a plasma concentration of riluzole of at least about 0.04 mcg/mL or more for about 24 hours or more. Preferably, the pharmaceutical composition is a controlled release composition. More preferably, the controlled release composition is a gastroretentive formulation or a multiparticulate formulation. In certain embodiments, the controlled release composition may include a dosage greater than 125 mg of riluzole.

In one aspect, the pharmaceutical composition comprising about 125 mg of riluzole provides a Cmax at steady state of less than about 0.3 mcg/mL for at least about 24 hours.

In another aspect, the pharmaceutical composition comprising about 125 mg of riluzole provides a Cmin at steady state of at least about 0.04 mcg/mL for at least about 24 hours.

In another aspect, the pharmaceutical composition comprising about 125 mg of riluzole provides an AUC at steady state of from about 1.5 mcg*h/mL to about 4 mcg*h/mL for at least about 24 hours. In some embodiments, the AUC at steady state is about 2.5 mcg*h/mL at least about 24 hours.

In some embodiments, the pharmaceutical composition is administered once a day. In some embodiments, the pharmaceutical composition is taken without food.

Another embodiment is a method of treating a CNS state comprising administering to a subject, preferably a human subject, in need thereof a composition as described in the preceding embodiment.

Another embodiment is a method of a treating a neurodegenerative or neuropsychiatric disorder comprising administering to a subject, preferably a human subject, in need thereof a composition as described in the preceding embodiment.

Another embodiment is a method of treating Alzheimer's disease, generalized anxiety disorder, obsessive compulsive disorder, spinocerebellar ataxia, or amyotrophic lateral sclerosis (ALS) comprising administering to a subject, preferably a human subject, in need thereof a composition as described in the preceding embodiment.

BRIEF DESCRIPTION OF THE DRAWINGS

FIGS. 11A and 11B shows simulated blood plasma concentration vs. time plots (FIG. 11A) for a 125 mg dose of a multiparticulate (no gastroretention) dosage form, while theoretical release profiles used in each simulation are shown for the gastroretentive dosage form (FIG. 11B).

DETAILED DESCRIPTION OF THE INVENTION

Figure 1:
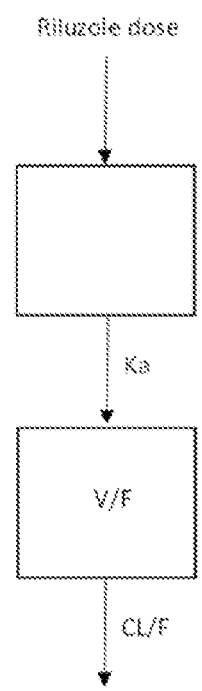
FIG. 1 shows the population PK model for immediate release riluzole published by Bruno et al.

Riluzole (Rilutek®) is a glutamate modulator drug that is indicated for the treatment of amyotrophic lateral sclerosis (ALS) at a dose of 50 mg twice daily. Doses must be taken at least 1 hour before or 2 hours after meals. Accordingly, there is an interest in developing a riluzole formulation that could be administered once daily rather than twice daily.

In addition to being useful to treat neurodegenerative diseases (such as Alzheimer's disease and ALS) and neuropsychiatric diseases, Riluzole may be used to treat other indications, such as spinal muscular atrophy and spinal cord injury and cancer. Furthermore, orally administered riluzole dosed twice a day at a total dose of 100 mg may relieve or treat neuropsychiatric symptoms and disorders, such as mood, anxiety disorder, refractory depression, obsessive-compulsive anxiety and the like. Despite being approved for ALS, extensively researched in neuropsychiatric disorders and commercially available for over 20 years, the clinically undesirable effects of riluzole have not been overcome and have limited its use.

Disclosed herein are controlled release formulations comprising riluzole or a pharmaceutically acceptable derivative thereof that are administered once a day. Potential advantages associated with a once a day formulation, such as the formulations disclosed herein, would include, but are not limited to, improved patient compliance, maintaining higher trough concentrations to improve efficacy, minimizing side effects (such as liver toxicity), and reducing inter-subject variability in PK parameters. In some embodiments, the side effects are minimized by avoiding high peak concentrations. In some embodiments, the controlled formulations disclosed herein may be taken with food. In some embodiments, the controlled formulations disclosed herein may be taken without food.

The development of the controlled release formulations described herein is based on a modeling and simulation approach to define an ideal concentration-time profile for a controlled release product. A population pharmacokinetic (PK) model for immediate release riluzole was used as a starting point. The development of PK models for simple (i.e., composed of a single slow absorption process) and mixed absorption processes (i.e., associated with a quick rise in concentrations followed by a slow-release) are discussed herein.

General Pharmacokinetics of Immediate Release Riluzole

The absolute bioavailability of riluzole is approximately 60%, and following oral administration, the product is absorbed rapidly with peak concentrations being reached between 0.75 to 1.6 h post-dose (European Medicines Agency (EMA), *Rilutek European Public Assessment Report (EPAR) Summary of Product Characteristics,* 2006; Abbara et al., *Br J Clin Pharmacol,* vol. 71, no. 3, pp. 403-410, March 2011; and van Kan et al., *Br J Clin Pharmacol,* vol. 59, no. 3, pp. 310-313, 2004). Over a dose range of 25 to 100 mg every 12 hours, the PK of riluzole appears to be dose proportional. The concomitant intake of food is associated with a decrease in the maximum concentration (Cmax) of approximately 45%, and a decrease in the area under the concentration-time curve (AUC) of around 20%, although the mechanism behind the food effect has not been clearly determined.

Riluzole is highly protein-bound, with plasma protein binding of ~95% to albumin and lipoproteins (Covis Pharmaceuticals, Rilutek product label, 2016; EMA 2006; and van Kan et al.). It is extensively distributed throughout the body, including crossing of the blood brain barrier, and is associated with a volume of distribution of around 245±69 L (3.4 L/kg) (EMA 2006 and van Kan et al.)

Following oral administration, at least 88% of the dose is metabolized. In vitro tests indicate that riluzole is mainly metabolized by CYP1A2 and glucuronidated by UGT-HP4 (Covis Pharmaceuticals 2016; EMA 2006; and van Kan et al.). A study conducted in 30 ALS patients also demonstrated a correlation between CYP1A2 activity and in vivo riluzole clearance (van Kan et al.). Some metabolites appear to exert pharmacological activity in vitro, but their in vivo activity is uncertain (Covis Pharmaceuticals 2016; EMA 2006; and van Kan et al.).

Excretion of riluzole occurs mainly via the urine (Covis Pharmaceuticals 2016; EMA 2006; and van Kan et al.). In fact, 90% of the dose is recovered in the urine, with 85% as glucuronides and 2% as unchanged riluzole (Covis Pharmaceuticals 2016; EMA 2006; and van Kan et al.). Fecal excretion accounts for 5% of the administered dose. The elimination half-life is reported to be, on average, 12 hours (ranging from 9 to 15 hours with a CV=35%) which leads to approximately 2-fold accumulation following repeated twice daily dosing (Covis Pharmaceuticals 2016; EMA 2006; and van Kan et al.).

Pharmacokinetics of Immediate Release Riluzole in Special Populations

Patients with mild and moderate hepatic impairment (according to the Child-Pugh scale) had increases in AUC (1.7-fold and 3-fold greater, respectively) compared to patients who had normal hepatic function (Covis Pharmaceuticals 2016; EMA 2006; and van Kan et al.).

The potential influence of race on riluzole exposure is unclear. The clearance of riluzole was reported to be 50% lower in male Japanese subjects compared to Caucasian subjects, even after normalizing for body weight (Covis Pharmaceuticals 2016). However, a clinical study comparing the PK of riluzole in healthy Japanese and Caucasian adult males concluded that there was no difference in mean PK parameters between both ethnic groups (EMA 2006 and van Kan et al.)

A PPK analysis was conducted using data from ALS patients and it showed that riluzole clearance was also influenced by the following covariates: total bilirubin, albumin, sex and smoking status (Sanofi-Aventis Canada, Rilutek product monograph, 2010). Analyses indicated that clearance was reduced in patients with increased bilirubin or decreased albumin levels, which likely reflected impaired hepatic function. Clearance in women was lower than in men (35.1 L/h vs. 51.4 L/h), and patients who were smokers had an enhanced clearance (36% higher clearance compared to non-smokers), which can be explained by the induction of CYP1A2.

Exposure Response Relationships for Immediate Release Riluzole

A dose-ranging trial that studied 959 patients with ALS demonstrated that patients who received 100 mg/day (50 mg twice daily) of riluzole had a statistically significant survival rate compared to placebo patients. Patients who received a higher daily dose of 200 mg/day did not have improved survival rates compared to the dose of 100 mg/day, but daily doses of 50 mg/day were not statistically different from placebo (EMA 2006).

In patients with traumatic spinal cord injuries (Grossman, et al, *J Neurotrauma*, vol. 31, no. 3, pp. 239-55, February 2014), those with cervical injuries (n=24) treated with riluzole had improved motor outcomes at 90 days post-injury, but no correlations could be made between response and Cmax. Peak riluzole levels were not as high as those observed in ALS patients receiving the same dose (50 mg twice daily), and PK assessments in other acute spinal injury patients (n=35) also suggested that riluzole exposure was lower in this population (Chow et al., *J Neurosurg Spine*, vol. 17, no. 1 Suppl, pp. 129-40, September 2012).

The relationship between exposure and adverse events was studied in a group of 169 patients with ALS who received the recommended dose of riluzole (Bruno et al., *Clin Pharmacol Ther*, vol. 62, no. 5, pp. 518-526, November 1997). This study suggested that higher exposure (i.e., serum levels and weight-adjusted AUC) was associated with an increased incidence of diarrhea but less fasciculations, and muscle stiffness. In other words, higher exposure led to an improvement in symptoms but a greater likelihood of experiencing side effects.

Controlled Release Formulations

The compositions described herein are controlled release formulations of riluzole or a pharmaceutically acceptable derivative thereof. In some embodiments, the compositions described herein are sustained release formulations of riluzole or a pharmaceutically acceptable derivative thereof. The phrase "pharmaceutically acceptable derivative thereof" in relation to riluzole includes pharmaceutically acceptable salts as well prodrug derivatives disclosed in any of U.S. Pat. Nos. 10,639,298, 10,562,870, 10,485,791, 10,357,497, and 9,725,427. Preferred prodrug derivatives of riluzole are N-methyl-2-(methylamino)-N-(2-oxo-2-((6-(trifluoromethoxy)benzo[d]thiazol-2-yl)amino)ethyl)acetamide; 2-(ethylamino)-N-methyl-N-(2-oxo-2-((6-(trifluoromethoxy)benzo[d]thiazol-2-yl)amino)ethyl)acetamide; 2-(isopropylamino)-N-methyl-N-(2-oxo-2-((6-(trifluoromethoxy)benzo[d]thiazol-2-yl)amino)ethyl)acetamide; 2-(tert-butylamino)-N-methyl-N-(2-oxo-2-((6-(trifluoromethoxy)benzo[d]thiazol-2-yl)amino)ethyl)acetamide; or a pharmaceutically acceptable form thereof.

Riluzole is a benzothiazole derivative of the following structure:

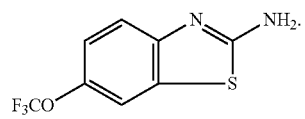

The chemical names for riluzole include 2-Amino-6-(trifluoromethoxy)benzothiazole and 6-(trifluoromethoxy)benzo[d]thiazol-2-amine. Riluzole has a molecular formula of $C_8H_5F_3N_2OS$, a molecular weight of 234.20, and a CAS number of 1744-22-5.

In some embodiments, the riluzole is in the form of a pharmaceutically acceptable salt. In some embodiments, pharmaceutically acceptable salt is obtained by reacting a compound described herein, such as riluzole, with an acid. In some embodiments, the riluzole (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, acetic acid; adipic acid; ascorbic acid (L); aspartic acid (L); benzenesulfonic acid; benzoic acid; camphoric acid carbonic acid; cinnamic acid; citric acid; ethanesulfonic acid; formic acid; fumaric acid; glutamic acid; glutaric acid; glycerophosphoric acid; glycolic acid; hippuric acid; isobutyric acid; lactic acid (DL), maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; salicylic acid; sebacic acid; stearic acid; succinic acid; sulfuric acid; tartaric acid (+L); thiocyanic acid; toluenesulfonic acid (p) and undecylenic acid. In some embodiments, the riluzole is prepared as a chloride salt, sulfate salt, bromide salt, mesylate salt, maleate salt, citrate salt, or phosphate salt. In some embodiments, the riluzole is prepared as an acetate, propionate, succinate, oxalate, benzoate, fumarate, maleate, or salicylate salt.

In some embodiments, the amount of riluzole present in the composition is from 75 about mg to about 300 mg, from about 90 mg to about 150 mg, from about 90 mg to about 135 mg, from about 100 mg to about 150 mg, from about 100 mg to about 140 mg, from about 100 mg to about 130 mg, from about 100 mg to about 125 mg, from about 110 mg to about 140 mg, from about 110 mg to about 130 mg, from about 110 mg to about 125 mg, from about 120 mg to about 130 mg, or from about 115 mg to about 135 mg. In some embodiments, the amount of riluzole present in the composition is about 75 mg, about 80 mg, about 85 mg, about 90 mg, about 95 mg, about 100 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg. In some embodiments, the amount of riluzole present in the composition is about 100 mg. In some embodiments, the amount of riluzole present in the composition is about 125 mg.

In some embodiments, the amount of the pharmaceutically acceptable salt of riluzole is present in the composition provides 75 about mg to about 200 mg, from about 90 mg to about 150 mg, from about 90 mg to about 135 mg, from about 100 mg to about 150 mg, from about 100 mg to about 140 mg, from about 100 mg to about 130 mg, from about 100 mg to about 125 mg, from about 110 mg to about 140 mg, from about 110 mg to about 130 mg, from about 110 mg to about 125 mg, from about 120 mg to about 130 mg, or from about 115 mg to about 135 mg of riluzole free base. In some embodiments, the amount of the pharmaceutically acceptable salt of riluzole present in the composition provides about 75 mg, about 80 mg, about 85 mg, about 90 mg, about 95 mg, about 100 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg of riluzole free base. In some embodiments, the amount of the pharmaceutically acceptable salt of riluzole present in the composition provides about 100 mg of riluzole free base. In some embodiments, the amount of the pharmaceutically acceptable salt of riluzole present in the composition provides about 125 mg of riluzole free base.

In some embodiments, the composition is administered once a day. In some embodiments, the compound is administered multiple times over the span of one day, which include two, three, or four times a day.

PK Parameters

The plasma concentration for riluzole preferably may be about from 0.03 mcg/mL to about 0.1 mcg/mL or more for about 1, 6, 8, 12, 24, 30, 36, 42, or 48 hours or more. The plasma concentration for riluzole preferably may be about from 0.03 mcg/mL to about 0.1 mcg/mL or more for about 24 hours or more.

The plasma concentration for riluzole may be at least about 0.03, 0.04, 0.05, 0.06, 0.07, 0.08, 0.09, 0.1, or 0.2 mcg/mL for at least about 1, 6, 8, 12, 24, 30, 36, 42, or 48 hours.

The plasma concentration for riluzole may be between 0.03 and 0.2 mcg/mL for at least about 1, 6, 8, 12, 24, 30, 36, 42, or 48 hours. The plasma concentration for riluzole may be between 0.03 and 0.2 mcg/mL for at least about 24 hours.

In some embodiments, the plasma concentration for riluzole represents an average plasma concentration level for a group of treated subjects and the time period of about 24 hours or more begins at any time point following administration. In some embodiments, the plasma concentration for riluzole of about 0.03 mcg/mL or more for a period of about 24 hours or more represents an average plasma concentration level for a group of treated subjects and the time period of about 24 hours or more begins at any time point following administration.

In some embodiments, the plasma concentration for riluzole represents the plasma concentration level for the individually treated subject and the time period of about 24 hours or more begins at any time point following administration to that subject. In some embodiments, the plasma concentration for riluzole of about 0.03 mcg/mL or more for a period of about 24 hours or more represents the plasma concentration level for the individually treated subject and the time period of about 24 hours or more begins at any time point following administration to that subject.

The Cmax at steady state for administration of riluzole may be less than about 0.3 mcg/mL. The Cmax at steady state for administration of riluzole may be about 0.3 mcg/mL or less. The Cmax at steady state for administration of riluzole may be about 0.05, 0.07, 0.1, 0.2, or 0.3 mcg/mL. In some embodiments, the Cmax at steady state for administration of riluzole may be about 0.07, 0.1, or 0.2 mcg/mL.

In some embodiments, the Cmax at steady state for riluzole of less than about 0.3 mcg/ml or more for a period of about 1 hour or more, including about 1, 6, 8, 12, 24, 30, 36, 42, or 48 hours. In some embodiments, the Cmax at steady state for riluzole of less than about 0.3 mcg/ml or more for a period of about 24 hours or more.

The Cmax for administration of riluzole may be less than about 0.3 mcg/mL. The Cmax for administration of riluzole may be about 0.3 mcg/mL or less. The Cmax for administration of riluzole may be about 0.05, 0.07, 0.1, 0.2, or 0.3 mcg/mL. In some embodiments, the Cmax for administration of riluzole may be about 0.07, 0.1, or 0.2 mcg/mL.

In some embodiments, the Cmax for riluzole of less than about 0.3 mcg/ml or more for a period of about 1 hour or more, including about 1, 6, 8, 12, 24, 30, 36, 42, or 48 hours. In some embodiments, the Cmax for riluzole of less than about 0.3 mcg/ml or more for a period of about 24 hours or more.

The Cmin at steady state for administration of riluzole may be about 0.03 mcg/mL or more. The Cmin at steady state for administration of riluzole may be about 0.03, 0.04, 0.05, 0.06, 0.07, 0.08, 0.09, or 0.1 mcg/mL.

In some embodiments, the Cmin at steady for riluzole of about 0.03 mcg/ml or more for a period of about 1 hour or more, including about 1, 6, 8, 12, 24, 30, 36, 42, or 48 hours. In some embodiments, the Cmin at steady for riluzole of about 0.03 mcg/ml or more for a period of about 24 hours or more. In some embodiments, the Cmin at steady for riluzole of about 0.04 mcg/ml or more for a period of about 24 hours or more.

The AUC at steady state for administration of riluzole may be about 1.5 mcg*h/mL or more. The AUC at steady state for administration of riluzole may be about 4 mcg*h/mL or less. The AUC at steady state for administration of riluzole may be from about 1.5 mcg*h/mL to about 4 mcg*h/mL. The AUC at steady state for administration of riluzole may be about 1.5, 2.0, 2.5, 3.0, 3.5 or 4 mcg*h/mL. In some embodiments, the AUC at steady state for administration of riluzole is about 2.5 mcg*h/mL.

In some embodiments, the AUC at steady state for riluzole of about 2 mcg*h/mL for a period of about 1 hour or more, including about 1, 6, 8, 12, 24, 30, 36, 42, or 48 hours. In some embodiments, the AUC at steady state for riluzole of about 2 mcg*h/mL for a period of about 24 hours or more.

The compositions of riluzole may be administered at least once per day. In some embodiments, the composition comprising riluzole is administered at least once per day. In some embodiments, riluzole is administered at least twice per day. In some embodiments, riluzole is administered one, two, three, four, or five times a day.

The composition of riluzole may provide improved patient compliance, maintaining higher trough concentrations to improve efficacy, minimizing side effects, and/or reducing inter-subject variability in PK parameters. In some embodiments, the side effects are minimized by avoiding high peak concentrations. In some embodiments, the composition of riluzole may be taken with food. In some embodiments, the composition of riluzole may be taken without food.

Pharmaceutical Compositions

The pharmaceutical composition described herein can be formulated for any type of administration that enables delivery of the riluzole to the site of action. Routes of administration include but are not limited to bronchial (e.g., by bronchial instillation), buccal, dermal (which may be or comprise, for example, one or more of topical to the dermis, intradermal, interdermal, transdermal, etc.), enteral, intraarterial, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc.

In some embodiments, the pharmaceutical compositions described herein are formulated for oral administration. Pharmaceutical compositions described herein can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. In some embodiments, the pharmaceutical compositions described herein are formulated as tablets, powders, pills, capsules, liquids, gels, syrups, slurries, or suspensions.

In some embodiments, the pharmaceutical compositions comprise riluzole and a pharmaceutically acceptable excipient. Excipients are pharmacologically inactive components, such as a carrier, diluent, lubricant, surfactant, or the like. Other examples of excipients include binders, coatings, disintegrants, barrier layer components, colouring agents, solubility enhancers, gelling agents, fillers, proteins, co-factors, emulsifiers, solubilising agents, suspending agents and mixtures thereof. A skilled artisan in the art would know what other pharmaceutically acceptable carriers and/or excipients could be included in the formulations described herein. The choice of excipients would depend on the characteristics of the compositions and on the nature of other pharmacologically active compounds in the formulation. Appropriate excipients are known to those skilled in the art (see Handbook Of Pharmaceutical Excipients, sixth edition, 2009 edited by Rowe et al., Pharmaceutical Press).

Examples of carriers include, but are not limited to, sugars, starches, cellulose and its derivatives, malt, gelatin, talc, calcium sulphate, vegetable oils, synthetic oils, polyols, alginic acid, phosphate buffered solutions, emulsifiers, isotonic saline, pyrogen-free water and combinations thereof.

Diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose; powdered cellulose, calcium carbonate, glycine, kaolin, mannitol, sodium chloride, inositol, bentonite, dextrose, dextrates, dextran, starches, pregelatinized starch, sucrose, xylitol, lactitol, mannitol, sorbitol, polyethylene glycol, and the like. Combinations of one or more diluents can also be used.

Lubricants and glidants are compounds that prevent, reduce or inhibit adhesion or friction of materials. Exemplary lubricants include, e.g., stearic acid, magnesium stearate, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, CabOSil®, a starch such as corn starch, silicone oil, a surfactant, and the like.

Surfactants include, but are not limited to, both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of olyoxyethylene sorbitane, sodium dioctylsulfosuccinate (DOSS), lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP®80 or SEPITRAP®4000 and mixtures thereof.

Suitable excipients may be, but not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, and/or polyvinyl-pyrrolidone (PVP). If desired, disintegrating agents may be combined as well, and exemplary disintegrating agents may be, but not limited to, cross-linked polyvinyl pyrrolidone, agar, or alginic acid or a salt thereof such as sodium alginate. The compositions may be prepared by any of the methods of pharmacy but all methods include the step of bringing into association one or more chemical agents as described above with the carrier which constitutes one or more necessary ingredients. In general, the pharmaceutical compositions described herein may be manufactured in conventional methods known in the art, for example, by means of conventional mixing, dissolving, granulating, dragee-making, levigating, emulsifying, encapsulating, entrapping, lyophilising processes and the like.

Pellet Core/Extended Release Coating Pharmaceutical Compositions

In another aspect, the present invention provides a pharmaceutical composition comprising or consisting of a pellet-in-capsule, wherein a pellet comprises a core that comprises a core seed with a mixture of riluzole and a binder coated onto the core seed, and an extended release coating surrounding the core comprising ethyl cellulose, a pore forming agent such as hydroxypropyl methyl cellulose or povidone, and a plasticizer.

In another aspect, the present invention provides a pharmaceutical composition for use in the methods of the aspects described above, wherein said composition is for oral administration and comprises a capsule for oral administration, said capsule comprising a plurality of pellets, each pellet comprising: (a) a pellet core comprising riluzole, or a pharmaceutically acceptable salt thereof, and (b) an extended release coating surrounding the pellet core.

In one embodiment, the extended release coating comprises ethyl cellulose and at least one of povidone and hydroxypropyl methyl cellulose, and a plasticizer. In a more specific embodiment, the extended release coating comprises ethyl cellulose, povidone, and a plasticizer.

In one embodiment, the pellet core comprises riluzole and a binder coated onto a core seed. In one embodiment, the core seed is a sugar sphere (nonpareil) or microcrystalline cellulose seed (e.g. CELPHERE™). In a more specific embodiment, the core seed is a microcrystalline cellulose core. In another specific embodiment, the core seed has a diameter in the range of 100 microns to 1,000 microns. In additional specific embodiments, the core seed has a diameter of 100, 200, 300, 400, 500, 600 or 700 microns. In preferred specific embodiments, the core seed has a diameter of less than 500 microns.

Combination Therapy

The compositions and methods disclosed herein may further comprise administering one or more additional therapies. The compositions disclosed herein may further comprise one or more additional therapies. The one or more additional therapies may be selected from active agents and drugs that relieve or reduce pain, such as oral pain.

Methods of Treatment

The formulations disclosed herein are useful for treating a variety of disorders and diseases, which include but are not limited to neurodegenerative diseases, neuropsychiatric disorders, and cancer. In some embodiments, the formulations are useful for treating neurodegenerative disorders, obsessive-compulsive and related disorders, affective disorders, and/or cerebellar disorders. Examples of such disorders include, but are not limited to, mild, moderate and severe Alzheimer's Disease, prodromal Alzheimer's Disease, amyotrophic lateral sclerosis (ALS), obsessive-compulsive disorder, trichotillomania, hoarding disorder, generalized anxiety disorder, social anxiety disorder, bipolar depression, spinocerebellar ataxia (SCA), Friederich's ataxia, sporadic ataxia, essential tremor and other ataxias. In some embodiments, the formulations are useful for treating amyotrophic lateral sclerosis (ALS), a pain disorder, traumatic spinal injury, cancer, spinocerebellar ataxia (SCA), Alzheimer's Disease (AD), obsessive compulsive Disorder (OCD), and generalized anxiety disorder (GAD). In some embodiments, the formulations disclosed herein are useful for treating a CNS state. In some embodiments, the formulations disclosed herein are useful for treating a neurodegenerative or a neuropsychiatric disorder. In some embodiments, the formulations disclosed herein are useful for treating Alzheimer's disease. In some embodiments, the formulations disclosed herein are useful for treating generalized anxiety disorder. In some embodiments, the formulations disclosed herein are useful for treating obsessive compulsive disorder. In some embodiments, the formulations disclosed herein are useful for treating spinocerebellar ataxia. In some embodiments, the formulations disclosed herein are useful for treating amyotrophic lateral sclerosis (ALS).

Other disorders and diseases contemplated for use include those related to central nervous system ("CNS") and/or depression/anxiety states, including neurodegenerative diseases. These include, but are not limited to, mania, attention deficit disorders, drug addiction, anxiety, bipolar depression, trichotillomania, bipolar disorder, treatment resistant and major depression, obsessive-compulsive disorder, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease.

In some embodiments, the disease may be a neuropsychiatric disorder. The term "neuropsychiatric disorder", as used herein, is a mental or neurologic disorder which is associated with the nervous system. In particular, the neuropsychiatric disorder may be anxiety disorders, generalized anxiety disorder, panic disorder, social anxiety, mood disorders, cognitive disorders, schizophrenia, dementia, vascular dementia, mixed dementia, agitation, apathy, anxiety, psychoses, post-traumatic stress disorders, irritability, disinhibition, learning disorders, memory loss, personality disorders, bipolar disorders, obsessive-compulsive disorders, autism, Rett syndrome, eating disorders, conduct disorders in DSM-5 and or combinations thereof The disease state may also include neurodegenerative disorders, pain disorders, ALS, cerebellar ataxia, hereditary ataxia, other ataxia, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, agitation in Alzheimer's disease, drug addiction, tinnitus, mental retardation, pseudobulbar affect, multiple sclerosis, Progressive Supranuclear Palsy, neuropathic pain, neuropathy, stroke, seizure, Fragile X, and the like.

In some embodiments, the disease may be a neuropsychiatric symptom. Neuropsychiatric symptoms include, but are not limited to, anxiety, depression, stress, fatigue, feelings of panic, fear, uneasiness, problems in sleeping, cold or sweaty hands and/or feet, mood liability, mania, impaired concentration or attention, cognitive problems, obsessions, compulsions, repetitive behaviors, aggression, social phobias or impairments, stage fright, shortness of breath, heart palpitations, an inability to be still and calm, dry mouth, numbness or tingling in the hands or feet, nausea, muscle tension, dizziness apathy, elation, disinhibition, irritability, wandering, irritable bowel, belly pain, belly discomfort, diarrhea, change in bowel habits, abdominal bloating, abdominal gas, abdominal bloating, constipation or combinations thereof. Additionally, neuropsychiatric symptoms could include: delusions, hallucinations, disorganized thinking or speech, derailment of focal topic or loose associations, incoherence, grossly disorganized or abnormal motor behavior (including catatonia), negative symptoms—reduced emotional expression, avolition, alogia, anhedonia, associality, dyskinesias (including tardive dyskinesia), anhedonia and dysphoria, anger and aggression, or symptoms of dissociation, or some combination thereof.

More specifically, neuropsychiatric disorders includes those listed in the Diagnostic and Statistical Manual of Mental Disorders (American Psychiatric Association, 5th Edition), such as neurodevelopmental disorders, intellectual disabilities, intellectual disability (intellectual developmental disorder), global developmental delay, unspecified intellectual disability (intellectual developmental disorder), communication disorders, language disorder, speech sound disorder, childhood-onset fluency disorder (stuttering), social (pragmatic) communication disorder, unspecified communication disorder, autism spectrum disorder, Rett Syndrome, attention deficit hyperactivity disorder (ADHD), unspecified attention-deficit/hyperactivity disorder, specific learning disorder, motor disorders, developmental coordination disorder, stereotypic movement disorder, tic disorders, Tourette's disorder, persistent (chronic) motor or vocal tic disorder, provisional tic disorder, other specified tic disorders, unspecified tic disorders, other neurodevelopmental disorders, unspecified neurodevelopmental disorders, schizophrenia spectrum and other psychotic disorders, delusional disorder, brief psychotic disorder, schizophreniform disorder, schizophrenia, schizoaffective disorder, major depressive or manic mood disorder concurrent with primary symptoms of schizophrenia, substance/Medication-induced psychotic disorder, psychotic disorder due to another medical condition, catatonia, other specified schizophrenia spectrum and other psychotic disorders, unspecified schizophrenia spectrum and other psychotic disorders, bipolar and related disorders, anxiety disorders, obsessive-compulsive and related disorders, trauma- and stressor-related disorders, reactive attachment disorder, disinhibited social engagement disorder, posttraumatic stress disorder, acute stress disorder, adjustment disorder, other specified trauma- and stressor-related disorders, unspecified trauma- and stressor-related disorders, dissociative disorders, dissociative identity disorder, dissociative amnesia, depersonalization/derealization disorder, somatic symptom disorders, encopresis, other elimination disorders, oppositional defiant disorder, intermittent explosive disorder, conduct disorder, disruptive, impulse-control and conduct disorders, other specified disruptive, conduct disorders, unspecified disruptive, and conduct disorders, substance-related and addictive disorders, substance-related disorders, alcohol-related disorders, alcohol use disorder, alcohol withdrawal, cannabis-related disorders, cannabis use disorder, gambling disorder, cluster A personality disorders, paranoid personality disorder, schizoid personality disorder, schizotypal personality disorder, cluster B personality disorders, antisocial personality disorder, borderline personality disorder, histrionic personality disorder, narcissistic personality disorder, cluster C personality disorders, avoidant personality disorder, dependent personality disorder, obsessive-compulsive personality disorder, and paraphilic disorders.

In some embodiments, the disease is cancer. Examples of cancer include, but are not limited to, Acute Lymphoblastic Leukemia (ALL), Acute Myeloid Leukemia (AML). Adrenocortical Carcinomas, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sezary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Wilms Tumor, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenstrom Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, Sqamous Cell Carcinoma, Squamous Neck Cancer with Occult Primary, Metastatic, Ttomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenstrom Macroglobulinemia. Wilms Tumor.

The treatment of the diseases and disorders as described herein are comprise the administration of any one of the formulations described herein to a subject in need thereof. Identifying the subject in need of such treatment can be in the judgment of the subject or a health care professional and can be subjective (e.g., opinion) or objective (e.g., measurable by a test or diagnostic method). The identified subject may be an animal or human in need thereof, particularly a human. Such treatment will be suitably administered to subjects, particularly humans, suffering from the disease or disorder.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "effective amount" or "therapeutically effective amount" refers to a quantity of riluzole sufficient to achieve a desired effect or a desired therapeutic effect. In the context of therapeutic applications, the amount of riluzole administered to the subject can depend on the type and severity of the disease or symptom and on the characteristics of the individual, such as general health, age, sex, body weight and tolerance to drugs. The skilled artisan will be able to determine appropriate dosages depending on these and other factors.

As used herein, the term "treatment" includes any treatment of a condition or disease in a subject, or particularly a human, and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. "Treatment," as used herein, could be used in combination with other standard therapies or alone.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

"Pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation.

EXAMPLES

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1: Pharmacokinetic Profile Model for Sustained Release Formulation

1. Objective

The objective of this study was to define an ideal pharmacokinetic profile for a once a day, sustained release riluzole formulation using modeling and simulations.

2. Methodology 2.1 Development of a Population PK Model for Sustained Release Riluzole A population PK model that had been developed for immediate release riluzole as described in Bruno et al. was used as a starting point. (Bruno et al., *Clin Pharmacol Ther*, vol. 62, no. 5, pp. 518-526, Nov 1997).

2.1.1 Population PK Model for Immediate Release Riluzole

The PK of immediate release riluzole was described by a one-compartment model with first-order absorption and first-order elimination. It is depicted in FIG. 1, and PK parameters associated with this model are presented in the Table 1 below.

TABLE 1

Final Population Estimates for Immediate Release Riluzole

| Population Parameter (THETA) | Estimate |
|---|---|
| CL/F (L/h) | 51.4 |
| Bilirubin | 0.888 |
| Albumin | −1.93 |
| Sex | 0.318 |
| Smoking | 0.363 |
| V/F (L/h) | 361 |
| Ka (1/h) | 5 |

| Variability Parameter (ETA) | Estimate |
|---|---|
| CL/F | |
| Inter-subject variability | 0.164 |
| Inter-occasion variability | 0.056 |
| V/F | |
| Inter-subject variability | 0.352 |
| Inter-occasion variability | 0.111 |
| Covariance between CL/F and V/F | 0.89 |

| Error Model Parameter (SIGMA) | Estimate |
|---|---|
| Proportional error | 0.0697 |

Source: adapted from Bruno et al.

This model included four covariates on clearance: total bilirubin, albumin, sex and smoking status. According to this model, riluzole clearance was greater in males compared to females, and it was also higher in smokers compared to non-smokers, likely due to the induction of CYP1A2. In patients with increased bilirubin or decreased albumin levels, clearance was reduced, presumably related to an impairment of hepatic function.

2.1.2 Population PK Model for Sustained Release Riluzole

The systemic parameters from the published immediate release (IR) model were used to construct a theoretical PPK model for sustained released riluzole. Covariates included in the IR model were also retained.

The first order absorption parameter (Ka) from the IR model was replaced with other absorption parameters (i.e., different Ka values) to mimic a sustained release absorption process. Two types of absorption processes were simulated. The first was a multiphasic modified-release absorption and the second was a simpler modified release formulation. Each is described in more detail below.

Multiphasic modified-release products have complex concentration-time profiles that are often characterized by multiple absorption peaks. An advantage of multiphasic modified-release is that a product can be formulated to have a fast-acting immediate component that is associated with faster onset of action (e.g., if a response is required within 2 hours post-dose), coupled with a slow-releasing extended release (ER) component that can maintain exposure throughout the day. The slow release component is typically formulated to start releasing drug before the end of the dosing interval associated with immediate release dosing. This type of formulation can also be beneficial for minimizing peak concentrations. Examples of products that fall under the multiphasic modified-release umbrella are extended-release methylphenidate (Concerta®) and extended-release zolpidem (Ambien® CR).

A more typical product is a "simpler" modified or sustained release formulation, where there is a single rise in concentrations, and where Cmax may occur some time after dosing. This type of absorption process can consist of a unique, slower absorption rate constant. This type of concentration-time profile is suitable when start of efficacy is not critical (i.e., when it is not important to achieve target concentrations rapidly), and when higher Cmax values do not pose any safety concerns.

Figure 2:
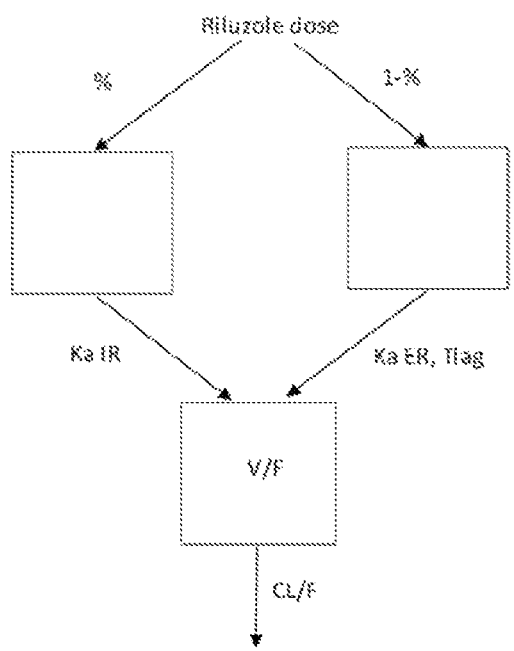
FIG. 2 shows the theoretical population PK model for multiphasic modified release riluzole.
Figure 3:
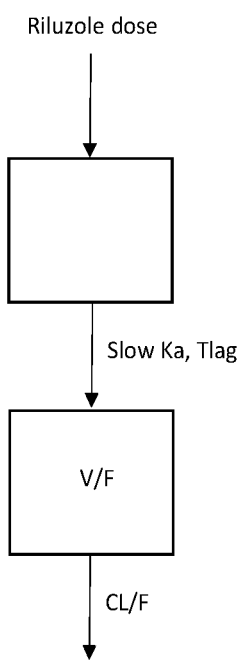
FIG. 3 shows the theoretical population PK model for simplified modified release riluzole.

Both types of sustained release models are depicted in FIG. 2 and FIG. 3.

2.2 Identification of Target Exposure

Riluzole exposure that is associated with a sustained release formulation must be within a pre-defined therapeutic interval to achieve a suitable balance between efficacy and toxicity.

The exposure associated with efficacy in ALS was determined from dose ranging studies in patients. These studies indicated that a dose of 100 mg/day (or 50 mg BID) was efficacious and that there was no benefit to administering higher doses as described in EMA 2006 (European Medicines Agency (EMA), Rilutek European Public Assessment Report (EPAR) Summary of Product Characteristics, 2006). Therefore, the steady-state exposure associated with this dosing regimen (AUC, Cmax, and Cmin) would be targeted by the sustained-release formulation.

Figure 4:
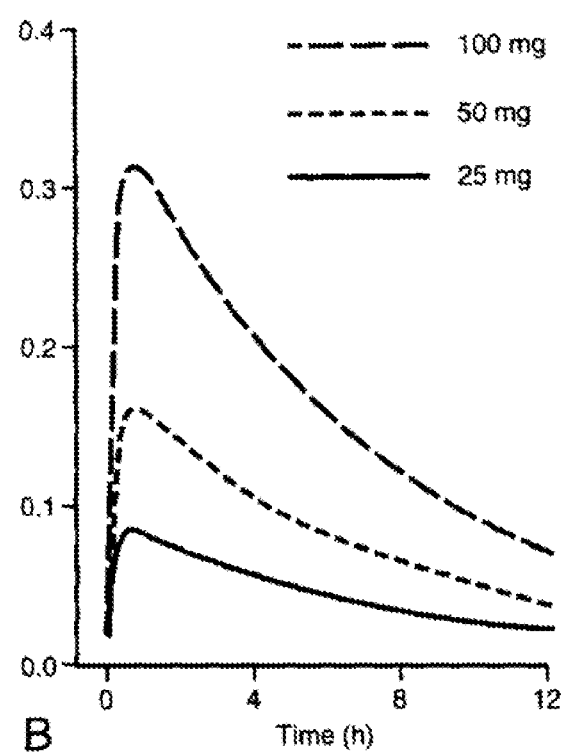
FIG. 4 shows the typical plasma profiles predicted for immediate release riluzole use in non-smoking males. Source: Bruno et al.
Figure 5A:
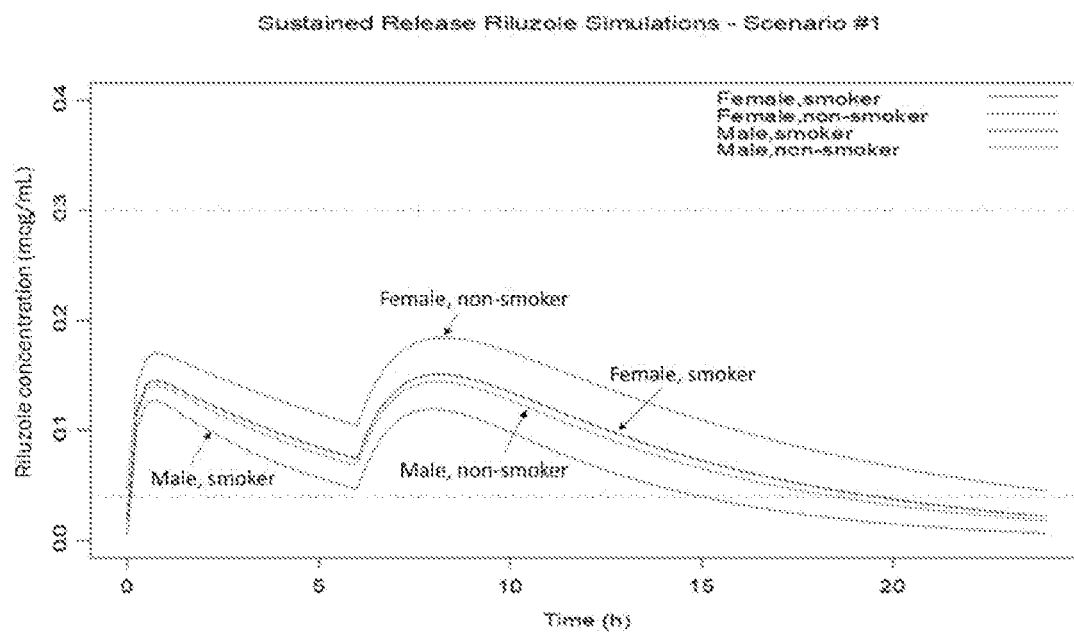
FIGS. 5A, 5B, 5C, 5D, 5E, 5F, 5G, 5H, 5I, 5J, 5K, 5L, and 5M show Scenarios #1, #2, #3, #4, #5, #6, #7, #8, #9, #10, #11, #12, and #13, respectively, for the simulated multiphasic and simplified release concentration-time profiles for riluzole.
Figure 5B:
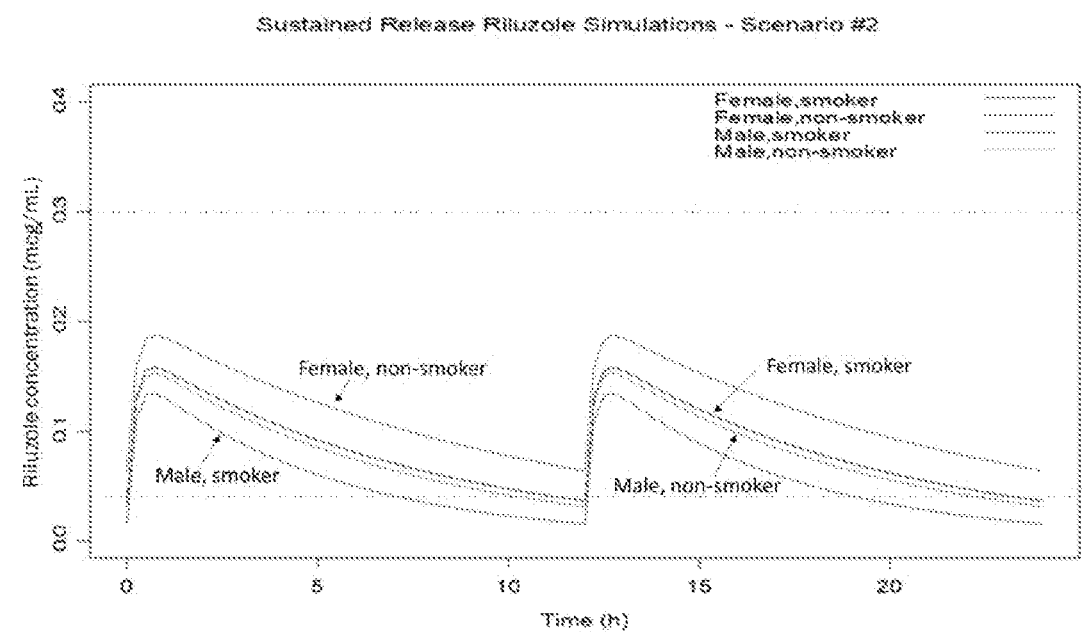
Figure 5C:
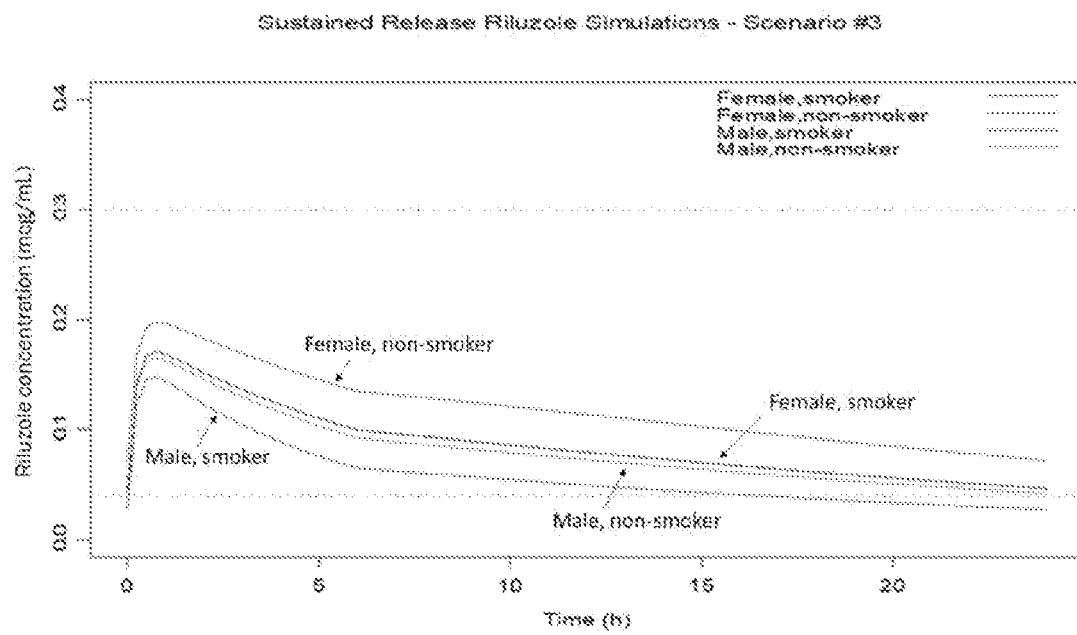
Figure 5D:
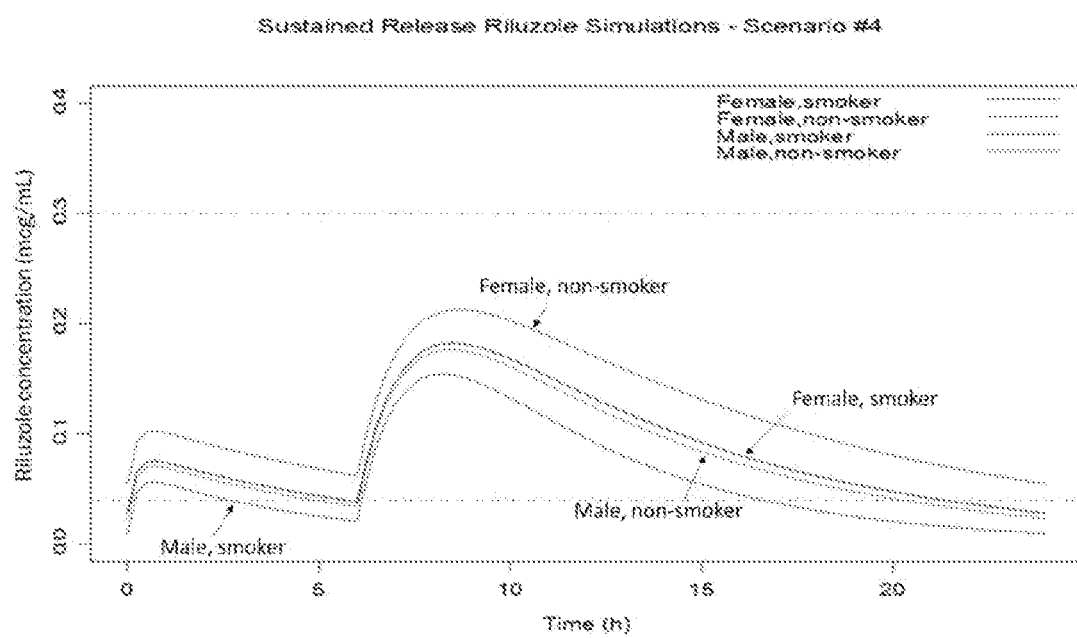
Figure 5E:
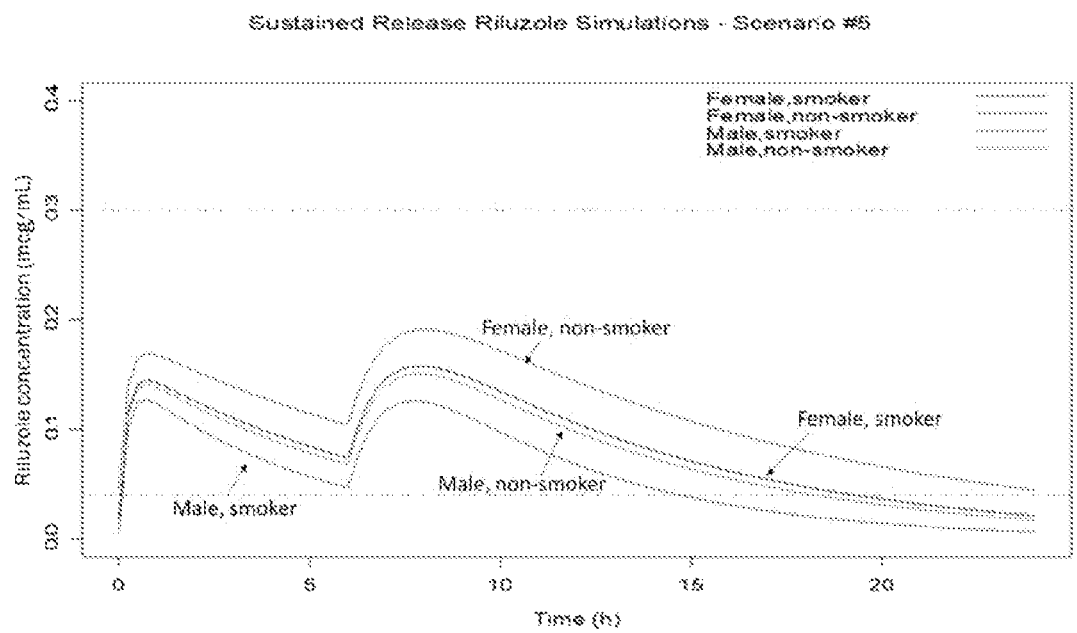
Figure 5F:
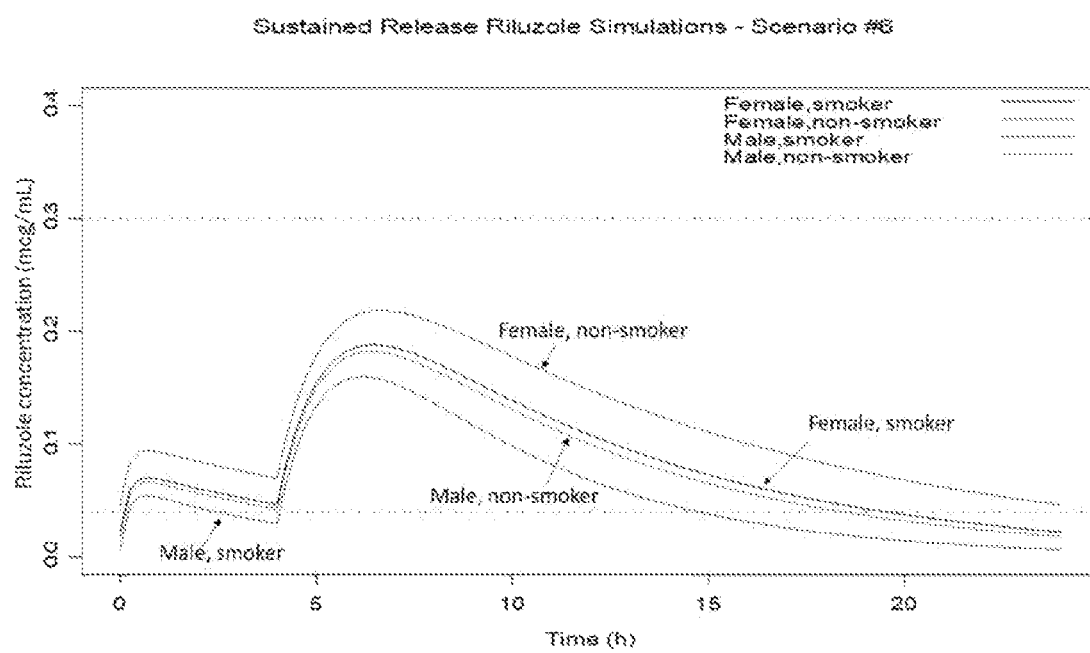
Figure 5G:
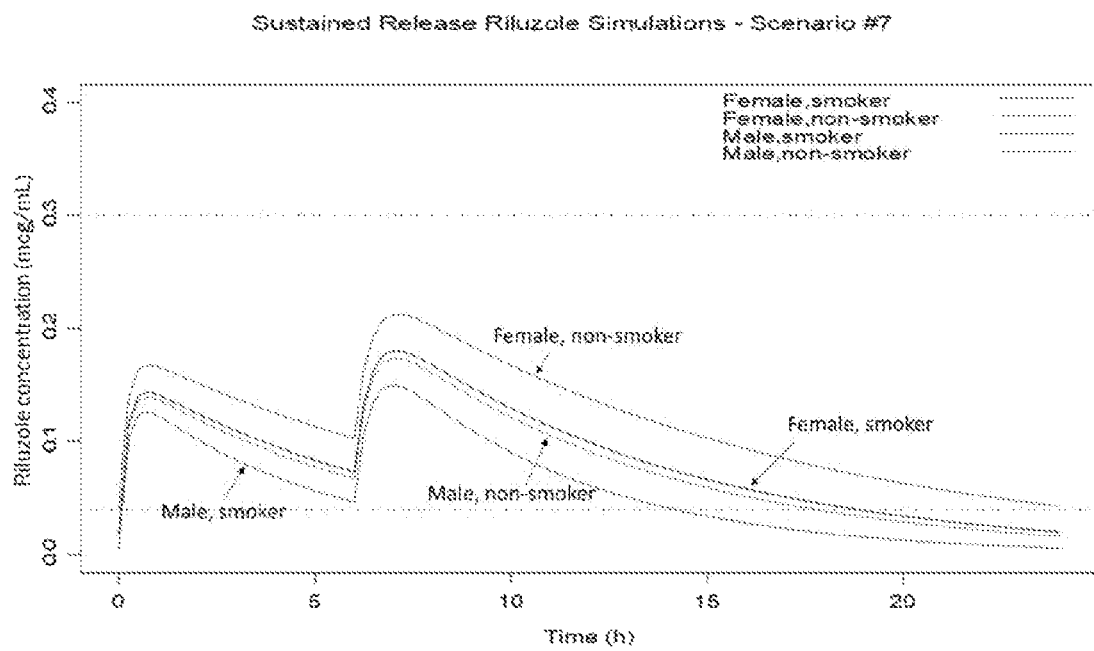
Figure 5H:
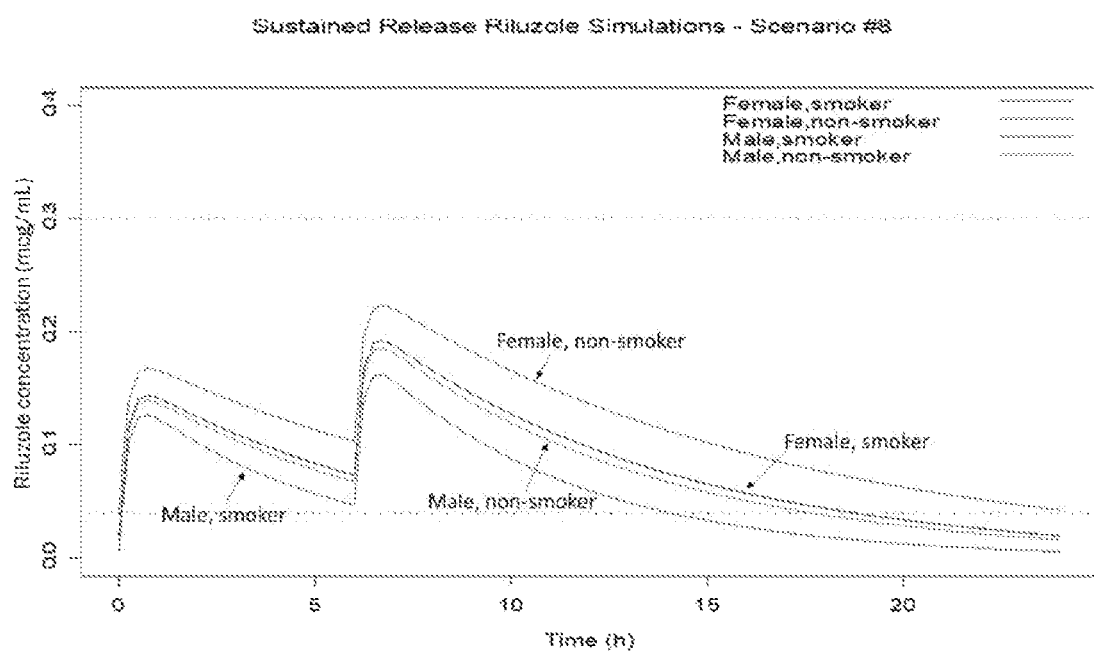
Figure 5I:
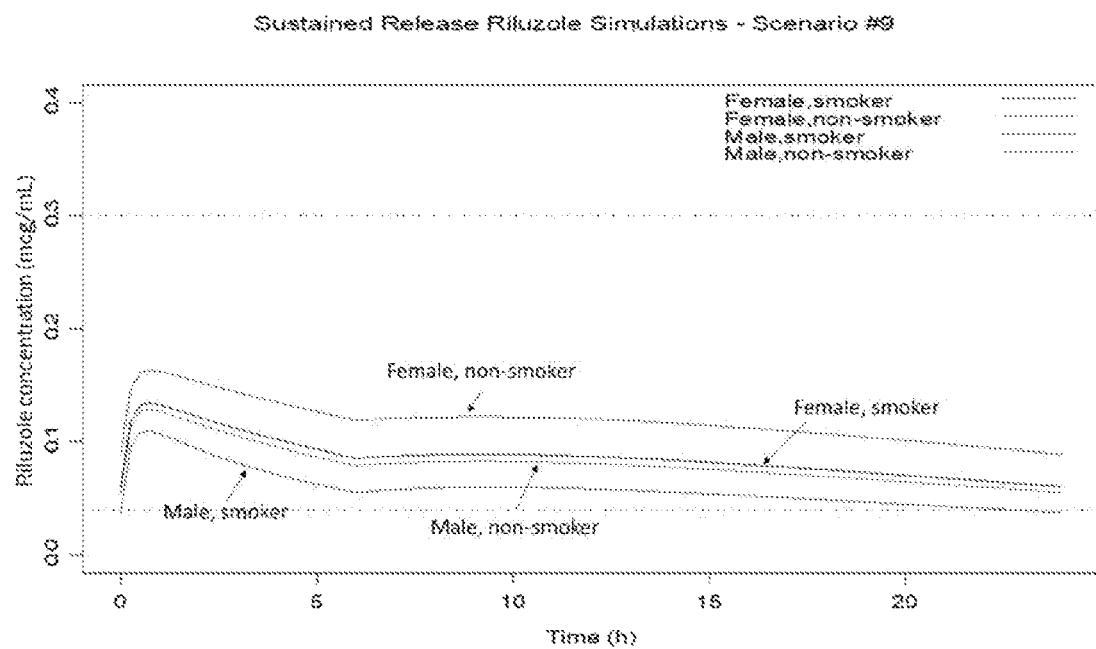
Figure 5J:
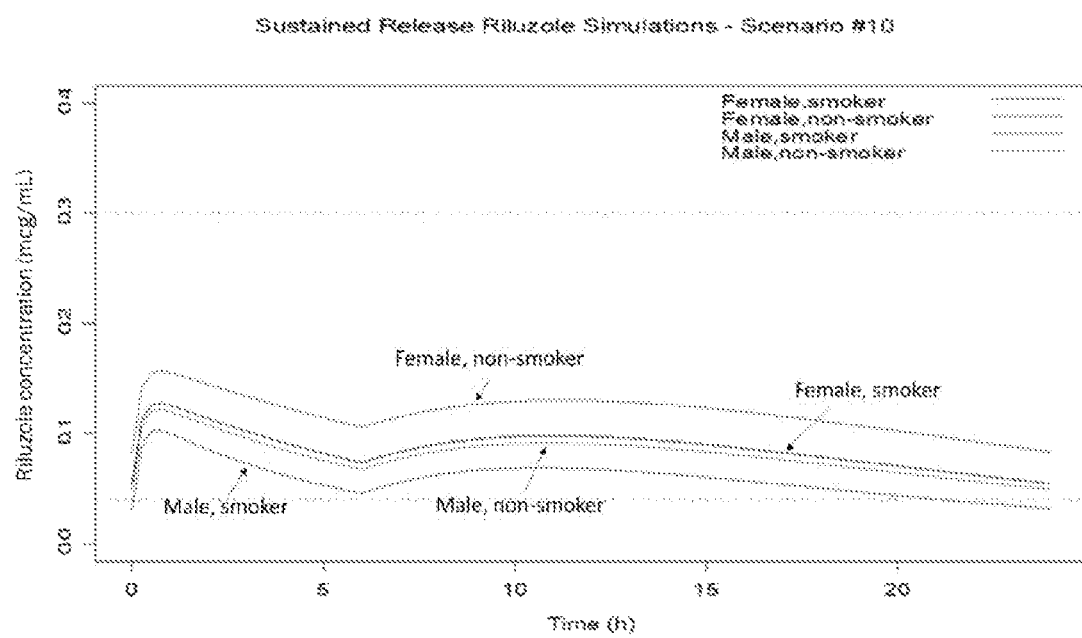
Figure 5K:
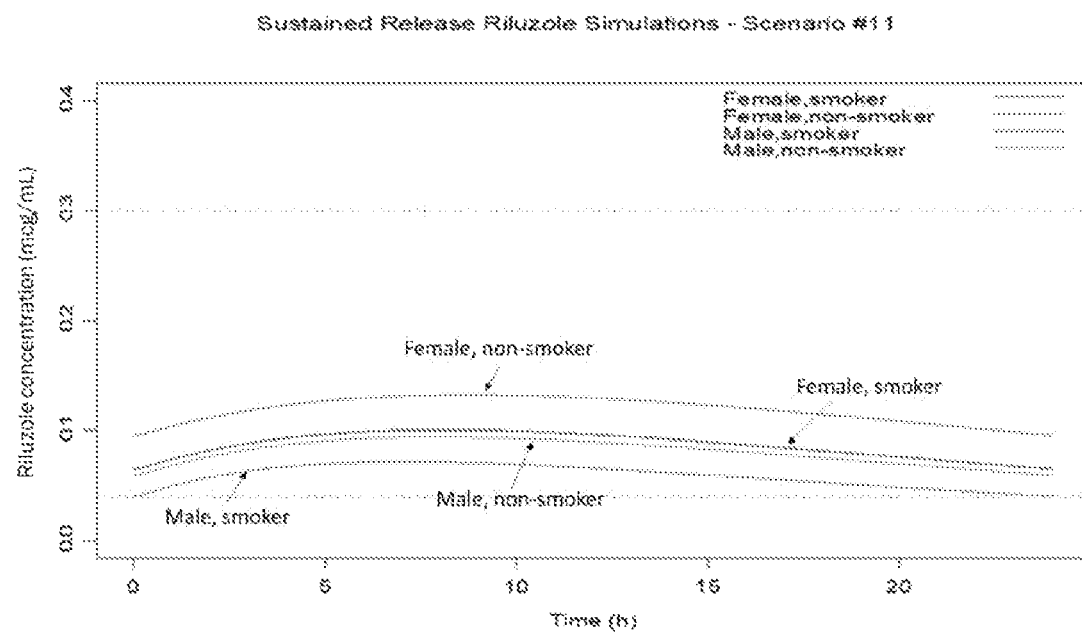
Figure 5L:
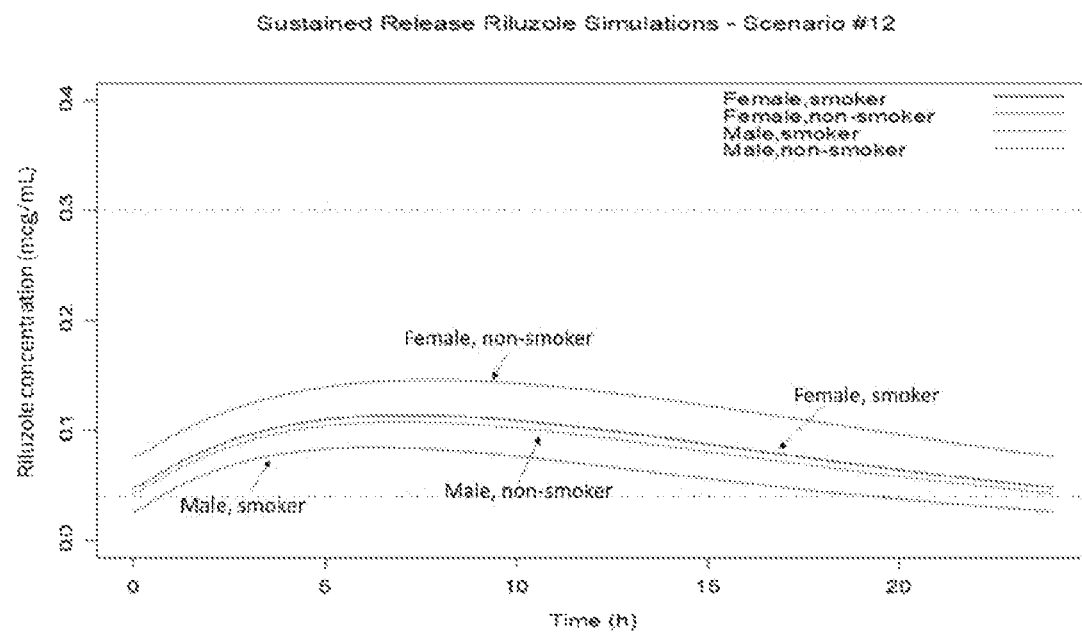
Figure 5M:
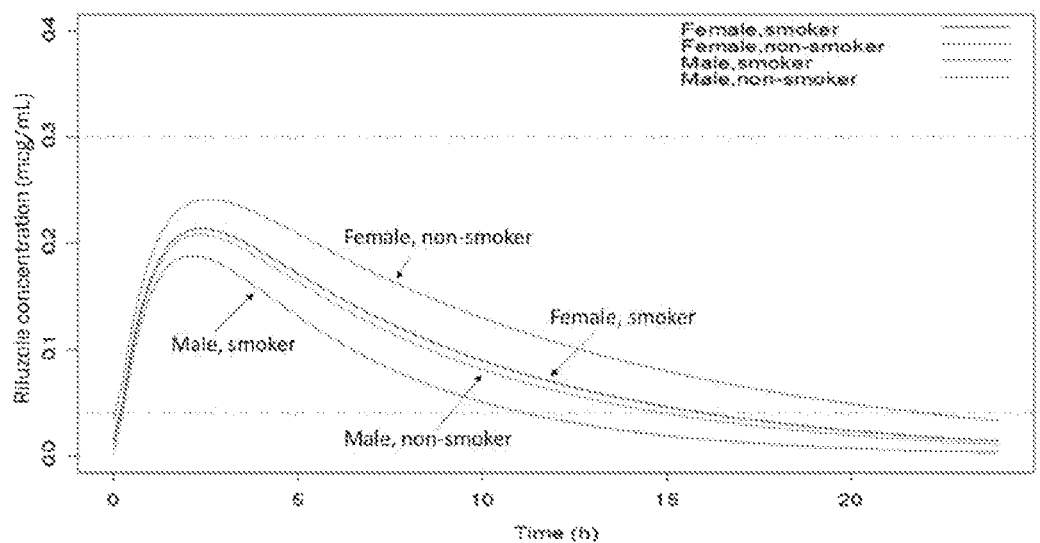

Plasma riluzole profiles associated with the immediate release product are presented in FIG. 4, for a dosing interval of 12 hours.

For a dosing regimen of 50 mg twice daily, the figure above suggests that trough concentrations in non-smoking males would be ~0.03 mcg/mL. Simulations of mean steady-state profiles in females (non-smoking and smoking) and smoking males indicated that trough concentrations could vary from ~0.02 to 0.07 mcg/mL following the administration of immediate release riluzole at a dose of 50 mg twice daily. Therefore, to ensure that efficacy is maintained, it would be reasonable to target trough values above 0.04 mcg/mL in all patients.

The 50 mg twice daily dosing regimen was associated with a steady-state daily AUC of approximately 2 mcgh/mL (ranging from around 1.5 mcgh/mL for male smokers to ~3 mcg.h/mL for female non-smokers). Therefore, an AUC of approximately 2 mcg·h/mL will be targeted.

Although a relationship between exposure and adverse events exists, with increased exposure being associated with the increased incidence of diarrhea as described in Groeneveld et al., there does not appear to be a clear maximal threshold for toxicity (Groeneveld et al., *Neurology*, vol. 61, no. 8, pp. 1141-1143, October 2003). A conservative approach was therefore used to determine maximal exposure with the goal of minimizing toxicity. As doses of up to 100 mg twice daily were well tolerated in the dose escalation study, exposure associated with a sustained release product should not exceed the exposure associated with this dosing regimen. This means that peak concentrations (i.e., Cmax) should be below ~0.3 mcg/mL.

Therefore, a sustained release riluzole formulation should aim to maintain the following steady-state parameters:
Cmin(ss) above 0.04 mcg/mL
Cmax(ss) below 0.3 mcg/mL
Overall daily exposure (i.e., AUCss) of around 2 mcg·h/mL, ranging from 1.5 mcg·h/mL to a maximum of 4 mcg·h/mL 1.3 Simulations For both types of modified-release products described in Section 1.1 (i.e., multiphasic modified release and simple modified release), various combinations of PK parameter estimates were simulated. For the multiphasic modified release products, different absorption rate constants (Ka) for IR and ER absorption were simulated, along with varying proportions of the dose that are absorbed by each type of absorption process. Different lag times (Alag) were also simulated.

Various estimates of Ka IR, Ka ER, Alag, and percentage that were tested are listed in Table 2 and the exposure associated with each combination of parameters was determined. Table 3 presents parameters that were tested for simple modified release profiles.

These simulations assumed that the riluzole product would be formulated to be free of any food effect. In other words, the administration of food was assumed to have no impact on the pharmacokinetics of the simulated sustained release riluzole formulations.

1.4 Assumptions

The population PK model developed for sustained release riluzole assumes that:
The systemic PK parameters (i.e., volume of distribution and clearance) are identical to those associated with immediate release riluzole
Inter-subject variability of PK parameters and residual variability are identical to those associated with immediate release riluzole
The absolute bioavailability is identical to the one for immediate release riluzole
The food effect between IR and SR formulations is the same
The safe and efficacious exposure for potentially treating other neurodegenerative diseases (like Alzheimer's disease) will be the same as for ALS 3. Results Predicted steady-state concentration time profiles for each of the simulated scenarios are presented in FIGS. 5A-5M. In each figure, dotted horizontal lines indicate the minimum trough value that is targeted (0.04 mcg/mL) and the concentration that should not be exceeded (0.3 mcg/mL).

TABLE 2

Absorption Parameter Estimates for Multiphasic Modified Release Riluzole

| Population Parameter | Multiphasic Modified Release Scenarios | | | | | | | | | |
|---|---|---|---|---|---|---|---|---|---|---|
| | 1 | 2 | 3 | 4 | 5 | 6 | 7 | 8 | 9 | 10 |
| Ka IR (l/h) | 5 | 5 | 5 | 5 | 5 | 5 | 5 | 5 | 5 | 5 |
| Ka ER (l/h) | 0.8 | 5 | 0.05 | 0.8 | 1 | 0.8 | 2.5 | 5 | 0.05 | 0.1 |
| % IR | 0.5 | 0.5 | 0.5 | 0.2 | 0.5 | 0.2 | 0.5 | 0.5 | 0.3 | 0.3 |
| % ER | 0.5 | 0.5 | 0.5 | 0.8 | 0.5 | 0.8 | 0.5 | 0.5 | 0.7 | 0.7 |
| Alag (h) | 6 | 12 | 6 | 6 | 6 | 4 | 6 | 6 | 6 | 6 |

TABLE 3

Absorption Parameter Estimates for Simple Modified Release Riluzole

| Population Parameter | Simple Modified Release Scenarios | | |
|---|---|---|---|
| | 11 | 12 | 13 |
| Ka ER (1/h) | 0.05 | 0.1 | 1 |
| Alag (h) | 0.1 | 0.1 | 0.1 |

Mean concentration-time profiles were simulated to steady-state using the software NONMEM v7.4.1. These simulations were performed using a daily dose of 100 mg for the following patient subgroups: smoking females, non-smoking females, smoking males and non-smoking males. If warranted by the results, doses exceeding 100 mg were tested.

The simulated concentration-time profiles showed that:
Concentrations never exceed 0.3 mcg/mL, therefore the hypothetical sustained release profiles should not pose any safety concerns
The concentration-time profiles associated with most scenarios fail to maintain concentrations above the lower threshold for the duration of the dosing period
Amongst the multiphasic modified release scenarios, Scenarios #9 and #10 appear to be associated with the most promising PK profiles, as concentrations remain above 0.04 mcg/mL for all subgroups except for male smokers
For the simple modified release scenarios, Scenario #11 is associated with concentrations that remain above targeted levels (0.04 mcg/mL) in all subgroups Predicted PK parameter estimates associated with the multiphasic and simple modified release scenarios are presented in Tables 4A, 4B, 4C, 5A and 5B. Cells that are marked with an asterisk (*) are values that meet the targets described in Section 1.2.

TABLE 4A

Simulated Mean Noncompartmental Parameter Estimates for Multiphasic Modified Release Riluzole-Simulated population PK parameters (Scenarios 1-10)

| Parameter | Multiphasic Modified Release Scenarios | | | | | | | | | |
|---|---|---|---|---|---|---|---|---|---|---|
| | 1 | 2 | 3 | 4 | 5 | 6 | 7 | 8 | 9 | 10 |
| Ka IR (l/h) | 5 | 5 | 5 | 5 | 5 | 5 | 5 | 5 | 5 | 5 |
| Ka ER (l/h) | 0.8 | 5 | 0.05 | 0.8 | 1 | 0.8 | 2.5 | 5 | 0.05 | 0.1 |
| % IR | 0.5 | 0.5 | 0.5 | 0.2 | 0.5 | 0.2 | 0.5 | 0.5 | 0.3 | 0.3 |
| % ER | 0.5 | 0.5 | 0.5 | 0.8 | 0.5 | 0.8 | 0.5 | 0.5 | 0.7 | 0.7 |
| Alag (h) | 6 | 12 | 6 | 6 | 6 | 4 | 6 | 6 | 6 | 6 |

M = male,
F = female

TABLE 4B

Simulated Mean Noncompartmental Parameter Estimates for Multiphasic Modified Release Riluzole-Predicted Noncompartmental PK parameters at Steady-State (Scenarios 1-5)

| Parameter | Multiphasic Modified Release Scenarios | | | | |
|---|---|---|---|---|---|
| | 1 | 2 | 3 | 4 | 5 |
| Cmax (ss) (mcg/mL) | | | | | |
| F, smoker | 0.151* | 0.159* | 0.171* | 0.182* | 0.158* |
| F, non-smoker | 0.185* | 0.188* | 0.198* | 0.213* | 0.191* |
| M, smoker | 0.127* | 0.135* | 0.148* | 0.154* | 0.127* |
| M, non-smoker | 0.144* | 0.153* | 0.166* | 0.176* | 0.151* |
| Cmin (ss) (mcg/mL) | | | | | |
| F, smoker | 0.0222 | 0.0365 | 0.0470* | 0.0281 | 0.0216 |
| F, non-smoker | 0.0456* | 0.0640* | 0.0724* | 0.0547* | 0.0448* |
| M, smoker | 0.0070 | 0.0156 | 0.0279 | 0.0095 | 0.0067 |
| M, non-smoker | 0.0183 | 0.0315 | 0.0425* | 0.0234 | 0.0177 |
| AUCtau (ss) (mcg.h/mL) | | | | | |
| F, smoker | 2.09* | 2.09* | 2.09* | 2.09* | 2.09* |
| F, non-smoker | 2.85* | 2.85* | 2.85* | 2.85* | 2.85* |
| M, smoker | 1.42 | 1.42 | 1.42 | 1.43 | 1.42 |
| M, non-smoker | 1.94* | 1.94* | 1.94* | 1.94* | 1.94* |

M = male, F = female, * = meets target

TABLE 4C

Simulated Mean Noncompartmental Parameter Estimates for Multiphasic Modified Release Riluzole-Predicted Noncompartmental PK parameters at Steady-State (Scenarios 6-10)

| Parameter | Multiphasic Modified Release Scenarios | | | | |
|---|---|---|---|---|---|
| | 6 | 7 | 8 | 9 | 10 |
| Cmax (ss) (mcg/mL) | | | | | |
| F, smoker | 0.188* | 0.180* | 0.192* | 0.134* | 0.127* |
| F, non-smoker | 0.218* | 0.212* | 0.223* | 0.164* | 0.157* |
| M, smoker | 0.160* | 0.150* | 0.162* | 0.109* | 0.103* |
| M, non-smoker | 0.182* | 0.174* | 0.185* | 0.129* | 0.122* |
| Cmin (ss) (mcg/mL) | | | | | |
| F, smoker | 0.0221 | 0.0203 | 0.0199 | 0.0609* | 0.0549* |
| F, non-smoker | 0.0462* | 0.0430* | 0.0425* | 0.0892* | 0.0835* |
| M, smoker | 0.0066 | 0.0060 | 0.0058 | 0.0379 | 0.0320 |
| M, non-smoker | 0.0181 | 0.0165 | 0.0162 | 0.0556* | 0.0496* |
| AUCtau (ss) (mcg.h/mL) | | | | | |
| F, smoker | 2.09* | 2.09* | 2.09* | 2.09* | 2.09* |
| F, non-smoker | 2.85* | 2.85* | 2.85* | 2.85* | 2.85* |
| M, smoker | 1.43 | 1.42 | 1.42 | 1.43 | 1.43 |
| M, non-smoker | 1.94* | 1.94* | 1.94* | 1.94* | 1.94* |

M = male, F = female, * = meets target

TABLE 5A

Simulated Mean Noncompartmental Parameter Estimates for Simple Modified Release Riluzole-Simulated population PK parameters (Scenarios 11-13)

| Parameter | Simple Modified Release Scenarios | | |
|---|---|---|---|
| | 11 | 12 | 13 |
| Ka IR(1/h) | — | — | — |
| Ka ER(1/h) | 0.05 | 0.1 | 1 |
| % IR | — | — | — |
| % ER | — | — | — |
| Alag (h) | 0.1 | 0.1 | 0.1 |

M = male, F = female

TABLE 5B

Simulated Mean Noncompartmental Parameter Estimates for Simple Modified Release Riluzole-Predicted Noncompartmental PK parameters at Steady-State (Scenarios 11-13)

| Parameter | Simple Modified Release Scenarios | | |
|---|---|---|---|
| | 11 | 12 | 13 |
| Cmax (ss) (mcg/mL) | | | |
| F, smoker | 0.1005* | 0.1138* | 0.2135* |
| F, non-smoker | 0.1324* | 0.1459* | 0.2414* |
| M, smoker | 0.0720* | 0.0850* | 0.1886* |
| M, non-smoker | 0.0942* | 0.1075* | 0.2083* |

TABLE 5B-continued

Simulated Mean Noncompartmental Parameter Estimates for
Simple Modified Release Riluzole-Predicted Noncompartmental
PK parameters at Steady-State (Scenarios 11-13)

| Parameter | Simple Modified Release Scenarios | | |
|---|---|---|---|
| | 11 | 12 | 13 |
| Cmin (ss) (mcg/mL) | | | |
| F, smoker | 0.0654* | 0.0485* | 0.0141 |
| F, non-smoker | 0.0954* | 0.0765* | 0.0334 |
| M, smoker | 0.0407* | 0.0268 | 0.0034 |
| M, non-smoker | 0.0598* | 0.0434* | 0.0111 |
| AUCtau (ss) (mcg.h/mL) | | | |
| F, smoker | 2.09* | 2.09* | 2.09* |
| F, non-smoker | 2.85* | 2.85* | 2.85* |
| M, smoker | 1.43 | 1.43 | 1.43 |
| M, non-smoker | 1.95* | 1.95* | 1.95* |

M = male, F = female, * = meets target

In all scenarios tested, the simulated exposure in male smokers was lower than in other subjects due to the male gender and positive smoking status which are associated with increased clearance. Hence, none of the simulated scenarios achieved target values in this subgroup, though Scenarios #9 and #10 were associated with the most promising PK characteristics amongst the multiphasic modified release profiles as the predicted Cmin(ss) were only slightly below the targeted values. For the simple modified release scenarios, Scenario #11 was the most promising, as all other exposure parameters met the target values in all subgroups.

Simulated results suggested that in order to achieve target AUCtau(ss) levels in all four subgroups, it would be necessary to administer a dose that was greater than 100 mg per day. Simulations for Scenarios #9, 10, and 11 were therefore repeated with daily doses of 125 mg, and results are presented in Tables 6A and 6B.

TABLE 6A

Simulated Mean Noncompartmental Parameter
Estimates for Promising Scenarios with Doses
of 150 mg-Simulated population PK parameters

| Parameter | Scenarios | | |
|---|---|---|---|
| | 9 | 10 | 11 |
| Simulated population PK parameters | | | |
| Ka IR (1/h) | 5 | 5 | — |
| Ka ER (1/h) | 0.05 | 0.1 | 0.05 |
| % IR | 0.3 | 0.3 | — |
| % ER | 0.7 | 0.7 | — |
| Alag (h) | 6 | 6 | 0.1 |

TABLE 6B

Simulated Population PK Parameter Estimates for Promising Scenarios
with Doses of 150 mg-Predicted Steady-State Parameters

| Parameter | Scenarios | | |
|---|---|---|---|
| | 9 | 10 | 11 |
| Cmax(ss) (mcg/mL) | | | |
| F, smoker | 0.168* | 0.159* | 0.1256* |
| F, non-smoker | 0.205* | 0.196* | 0.1655* |
| M, smoker | 0.137* | 0.128* | 0.0900* |
| M, non-smoker | 0.161* | 0.152* | 0.1178* |
| Cmin(ss) (mcg/mL) | | | |
| F, smoker | 0.0761* | 0.0687* | 0.0818* |
| F, non-smoker | 0.1115* | 0.1044* | 0.1192* |
| M, smoker | 0.0474* | 0.0400* | 0.0509* |
| M, non-smoker | 0.0695* | 0.0620* | 0.0747* |
| AUCtau(ss) (mcg · h/mL) | | | |
| F, smoker | 2.61* | 2.61* | 2.62* |
| F, non-smoker | 3.56* | 3.56* | 3.57* |
| M, smoker | 1.78* | 1.78* | 1.78* |
| M, non-smoker | 2.43* | 2.43* | 2.43* |

An ideal multiphasic modified release riluzole product would have the following characteristics:
  Two first-order absorption processes, with the fastest one being equal to 5 $h^{-1}$ and the slower rate ranging from 0.05 to 0.1 $h^{-1}$
  Approximately 70% of the administered dose would be absorbed at the slower rate, and there should be a lag time of approximately 6 hours before this absorption starts
  There would be no lag time on the fast absorption rate constant An ideal simple modified release riluzole product could have an absorption rate constant of 0.05 $h^{-1}$ with a negligible lag time of 0.1 hours.

For both multiphasic and simple modified release riluzole formulations, daily doses of 100 mg would be adequate to achieve target exposure levels in females (regardless of smoking status) and in non-smoking males. However, if the intent is to develop a product that can be administered at the same dose for all patients, a daily dose of 125 mg would be necessary.

4. Conclusions

A previously developed population PK model for immediate release riluzole was adapted to simulate potential sustained-release profiles that would allow once-daily dosing of riluzole.

Various combinations of PK parameters were simulated. Simulations suggested that it would be possible to achieve a potentially safe and efficacious exposure in females and non-smoking males if a modified release product had the following characteristics:
  Multiphasic modified release: One fast absorption rate constant of 5 $h^{-1}$ with no lag time, accounting for 30% administered dose's absorption, and one slow absorption rate constant ranging from 0.05 to 0.1 $h^{-1}$ with a lag time of 6 hours, accounting for 70% administered dose's absorption OR
  Simple modified release: A single slow absorption rate constant of 0.05 $h^{-1}$ with a lag time of 0.1 hours For both multiphasic and simple modified release riluzole formulations, daily doses of 100 mg would be adequate to achieve target exposure levels in females (regardless of smoking status) and in non-smoking males. However, if the intent is to develop a product that can be administered at the same dose for all patients, a daily dose of 125 mg would be necessary.

Example 2—Simulated Controlled Release
Formulations of Riluzole Achieving Targets Riluzole is prescribed to treat patients with amyotrophic lateral sclerosis (ALS). The current reference listed drug product (RLD) is a 50 mg film coated immediate release tablet dosed twice daily. The RLD has an oral bioavailability of 60%, is dose linear up to 100 mg in vivo, and has a known negative food effect (45% and 20% decrease in Cmax and AUC when taken with a meal, respectively). As such, it is prescribed to be taken one hour before or two hours after a meal to avoid a loss in exposure. Riluzole is also known to exhibit increased side effects due to liver toxicity when prescribed to patients with some level of liver impairment and in some cases for patients without history of liver disease, suggesting overexposure of riluzole to these patients could be harmful. The focus of the modeling work herein was to evaluate the opportunity for an improved product of riluzole that achieves a once daily dosing regimen within a modified release (MR) dosage form architecture. Additionally, it would be beneficial to the patient and patient compliance if the dependence on prandial state was removed and the new product could be taken without regard to meals. Lastly, a slower absorption rate into systemic circulation accomplished via modified release may be beneficial to patients with liver impairment and in patients with no prior liver disease given the levels of drug introduced to the liver over time are lower than what is seen from the immediate release BID treatment.

A GastroPlus v9.7 (Simulations Plus, Inc.) simulated model (the underlying assumptions used for the model are discussed at the end of this example) was used to establish controlled release formulations that could accomplish the following target pharmacokinetic profile (TPP):
  (a) With crystalline or amorphous drug, achieve a once daily dosing regimen with a steady state AUC over the course of 24 hours>1.5 µg h/mL (target 2 µg h/mL, a Cmax at steady state of <0.3 µg/mL and a Cmin at steady state of >0.04 µg/mL.
  (b) No, or clinically insignificant, food effect.

Both gastroretentive and traditional modified release via multiparticulate platforms were explored for achieving the above goals. The simulations suggest that both architectures may achieve these goals with achievable drug release profiles. For purposes of achieving the desired pharmacokinetic profile, the gastroretentive approach may be preferred due to less reliance on riluzole colonic absorption. Certain modified release dosage forms that do not retain in the stomach might require greater colonic absorption given that longer release rates are required to achieve the TPP. Given the presence and origin of the negative food effect for riluzole, distal GI absorption for riluzole may be harder to achieve, and therefore, the formulations discussed herein are modified to reduce reliance on colonic absorption.

The following specifications are preferred examples for each dosage form type:
  (a) A gastroretentive dosage form that remains in the stomach throughout the drug release profile with a time to 80% drug release ("T80") of 14 to 18 hours. If the dosage form does not provide gastroretention throughout the entire release profile, a minimum retention time of approximately 4-6 hours can still maintain the steady state target of 2 hr/mL and a Cmin of 0.04 µg/mL. For this formulation, crystalline riluzole is preferred as the drug substance.
  (b) A multiparticulate (or other traditional modified release architectures such as osmotic push/pull or matrix tablet) dosage form that has a T80 of 14 to 18 hours. For these formulations, amorphous riluzole is preferred to avoid incomplete absorption of the administered dose in the colon. However, restricted absorption due to gastrointestinal transit time may still be a factor regardless of ingested drug form. An alternative embodiment would therefore utilize an increase in the loading dose of riluzole to >125 mg to get more total riluzole (mg) absorbed during the course of GI transit since it is unlikely the drug will be solubility limited.

Simulations were performed using a physiologically based pharmacokinetic model (PBPK) to capture differences in liver metabolism, tissues volumes and perfusion rates for healthy, geriatric healthy, and impaired liver function populations. The results suggest that if the target product profile is maintained and liver toxicity is a result of maximum concentrations achieved in the liver (Cmax) rather than chronic exposure over time (AUC), then the modified release dosage forms herein optionally may benefit both healthy patients and patients with some level of liver impairment or patients with no prior liver disease history through one or more possible benefits including but not limited to reduced liver Cmax at steady state and is not expected to introduce differences in exposure for geriatric populations compared to the current product on the market. In addition, the formulations herein may be optionally given once a day (or at a reduced frequency) without regard to when the patient has a meal. Optionally, the formulations may be in a form that is easier to swallow than existing formulations of riluzole.

Simulation Results

For riluzole, drug absorption is likely not an issue if drug is mostly absorbed in the upper small intestine. If colonic absorption is utilized, risk of incomplete absorption increases from a modified release dosage form that releases too large of the drug fraction in the colon.

Figure 6:
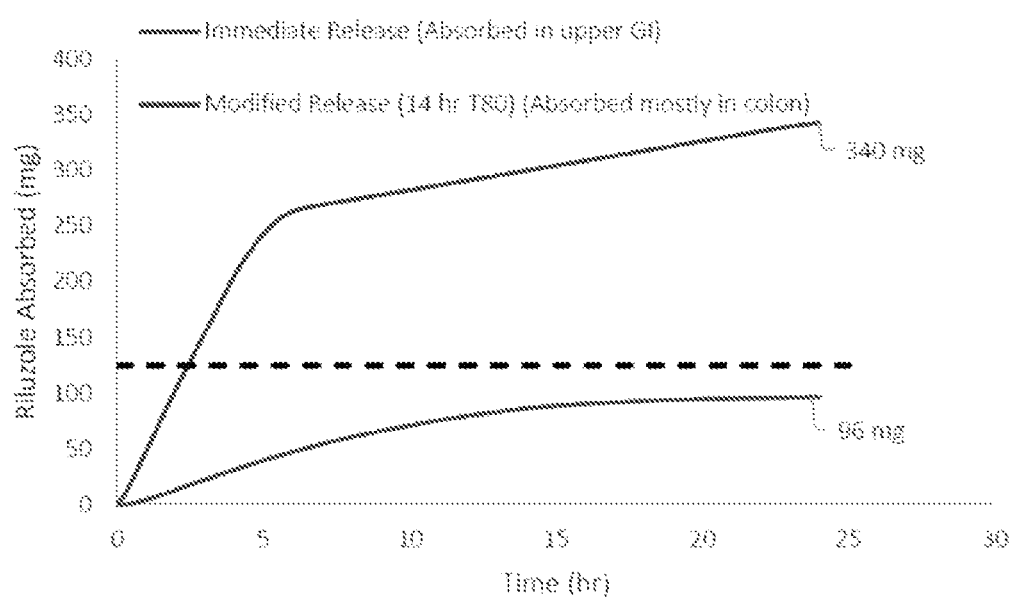
FIG. 6 shows mass absorbed vs. time simulation using the model of example 2 for riluzole.

Given the fact that to achieve a once daily dosing regimen, a single dose of riluzole needs to increase at least 2 fold to achieve a similar steady state AUC to the RLD BID treatment (2-fold reduction in dosing frequency=2 fold increase in dose). Therefore, an assessment was performed as to whether or not the maximum absorbable dose of riluzole will permit complete absorption up to the target dose of 125 mg. Using the model framework established for riluzole and summarized in the absorption model summary, the simulation in FIG. 6 suggests that absorption is not a barrier for crystalline riluzole up to the target dose if it can absorb mostly in the proximal small intestine, showing at least 340 mg as a maximum absorbable dose. If the formulation requires colonic absorption, this likely introduces some risk of incomplete absorption at the target dose.

Figure 7A:
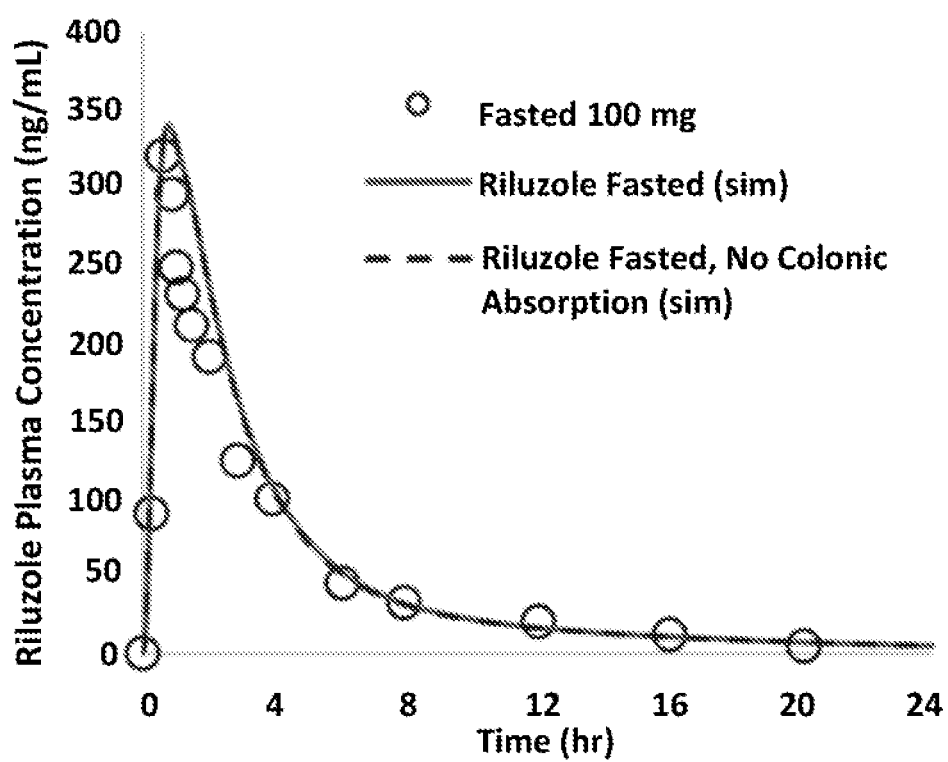
FIGS. 7A and 7B shows Simulated vs. observed riluzole blood plasma concentration vs. time plots for the fed (FIG. 7B) and fasted (FIG. 7A) state at a 100 mg dose.
Figure 7B:
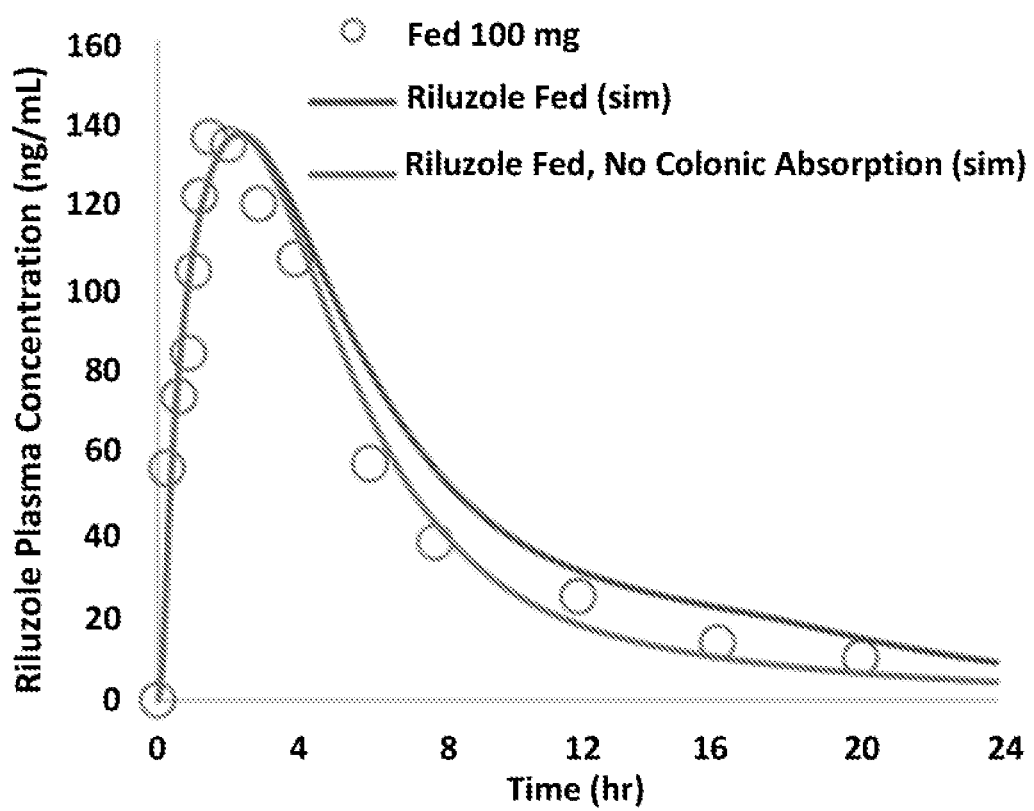

The negative food effect exhibited by riluzole is likely due to incomplete absorption (not metabolism related). Riluzole exhibits a negative food effect when taken with a meal, with a mean drop in Cmax and AUC of 45% and 20%, respectively. While modest, it is defined in the product label that the medication should not be taken within 1 hour before or 2 hours after a meal. This introduces patient compliance issues as well as overall patient perception of the medication. The food effect may be driven by a decreased permeability of riluzole in the fed state. This is likely driven by the sequestration of free drug into fats/bile salt micelles, driving the effective permeability to a lower value. Based on the possibility that the permeability of riluzole is as much as 3.5 times lower in the fed state compared to the fasted state, simulations were performed with the adjusted permeability for fed state and compared to the observed data for fasted and fed performance at a 100 mg dose produced by Le Liboux et al. (J Clin. Pharmacol 1997; 37:820-827). Simulations shown in FIG. 7 and tabulated data in table 7 show good agreement with observed data, suggesting the food effect is potentially driven by the assumptions of the model. Additionally, the data is in best agreement when there is no colonic absorption, suggesting that it is possible that part of the negative food effect (and resulting incomplete absorption) is also driven by poor colonic absorption of riluzole, in agreement with similar risks highlighted in FIG. 6 for a modified release dosage form relying on absorption in the colon.

TABLE 7

Tabulated data for riluzole blood plasma concentration vs. time plots for the fed and fasted state at a 100 mg dose. Observed data extracted from the Le Liboux et al. study.

| Treatment | Cmax (ng/mL) | AUC (0-inf) ng hr/mL | Tmax (hr) | % Abs |
|---|---|---|---|---|
| Fasted (observed) | 387 | 1269 | 0.8 | 100 |
| Fed (observed) | 216 | 1047 | 2 | 80 |
| Fasted (simulated) | 340 | 1327 | 0.8 | 100 |
| Fasted (simulated w/o colon absorption) | 340 | 1315 | 0.8 | 99 |
| Fed (simulated) | 137 | 1179 | 2.3 | 95 |
| Fed (simulated w/o colon absorption) | 137 | 1007 | 2.3 | 76 | mitigated with a gastroretentive dosage form, with only a modest impact on Cmax (12% decrease) and no impact on AUC (<1% decrease). This may achieve the TPP and improve patient compliance through a more flexible dosing regimen—i.e., once daily without regard to meals.

TABLE 8

Tabulated data for simulations comparing plasma concentration vs. time plots (top) for a 125 mg dose of a gastroretentive dosage form. SS = steady state

| Dose (mg) | Release Description | % MR | AUC (24 hr, SS) | Cmax (ng/ml) SS | Cmin (ng/ml), SS | % Dose Absorbed |
|---|---|---|---|---|---|---|
| 125 | 14 Hr T80 | 100 | 2062 | 123 | 40 | 95 |
| 125 | 18 Hr T80 | 100 | 1979 | 106 | 46 | 89 |
| 125 | 22 Hr T80 | 100 | 1891 | 93 | 49 | 83 |
| 125 | 30% IR/70% MR 0.3/10 Hr T80, 6 hr MR delay[10] | 70 | 2074 | 169 | 39 | 95 |

Figure 9:
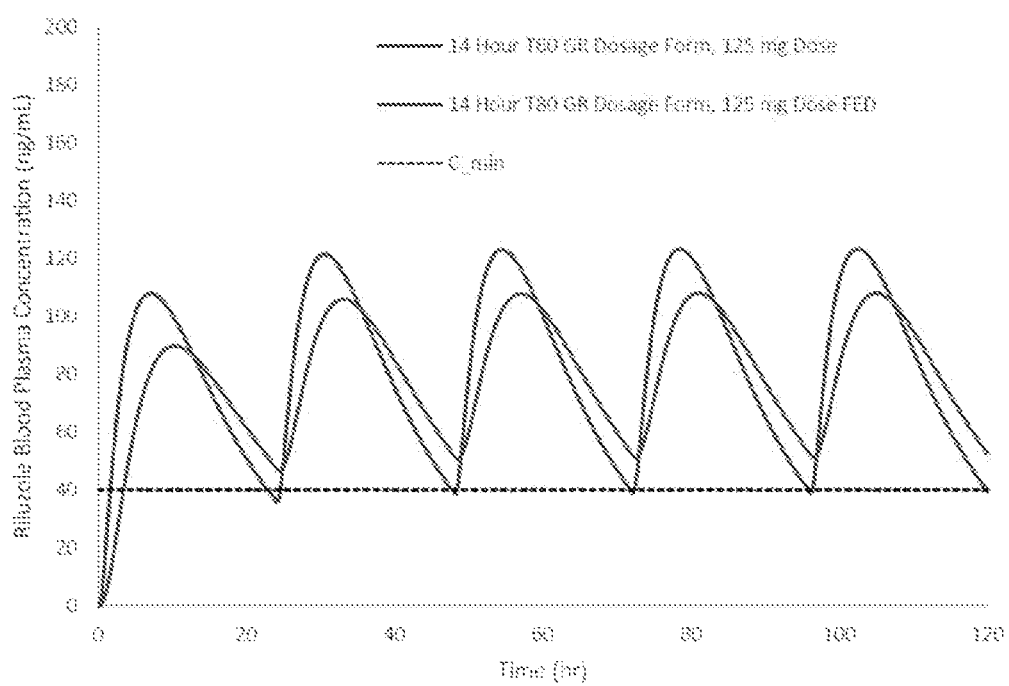
FIG. 9 shows simulated blood plasma concentration vs. time plots in the fasted and fed state for a 125 mg dose of a gastroretentive dosage form that remains in the stomach throughout the entire release profile.

FIG. 9 and Table 9 show a plotted simulation for plasma concentration versus time and tabulated data respectively for a 125 mg dose of a gastroretentive formulation in the fasted and fed states. SS=steady state

TABLE 9

Tabulated data for simulations comparing plasma concentration vs. time plots (top) for a 125 mg dose of a gastroretentive dosage form in the fasted and fed state. SS = steady state

| Prandial | Dose (mg) | Release Description | % RM | AUC (24 hr SS) | Cmax (ng/mL), SS | Cmin (ng/mL), SS | AUC Ratio (Fed/ Fasted) | Cmax Ratio (Fed/ Fasted) | Cmin Ratio (Fed/ Fasted) |
|---|---|---|---|---|---|---|---|---|---|
| Fasted | 125 | 14 Hr T80 | 100 | 2062 | 123 | 40 | 0.99 | 0.88 | 1.15 |
| Fed | 125 | 14 Hr T80 | 100 | 1979 | 106 | 46 | | | |

Gastroretentive Formulation

Figure 8A:
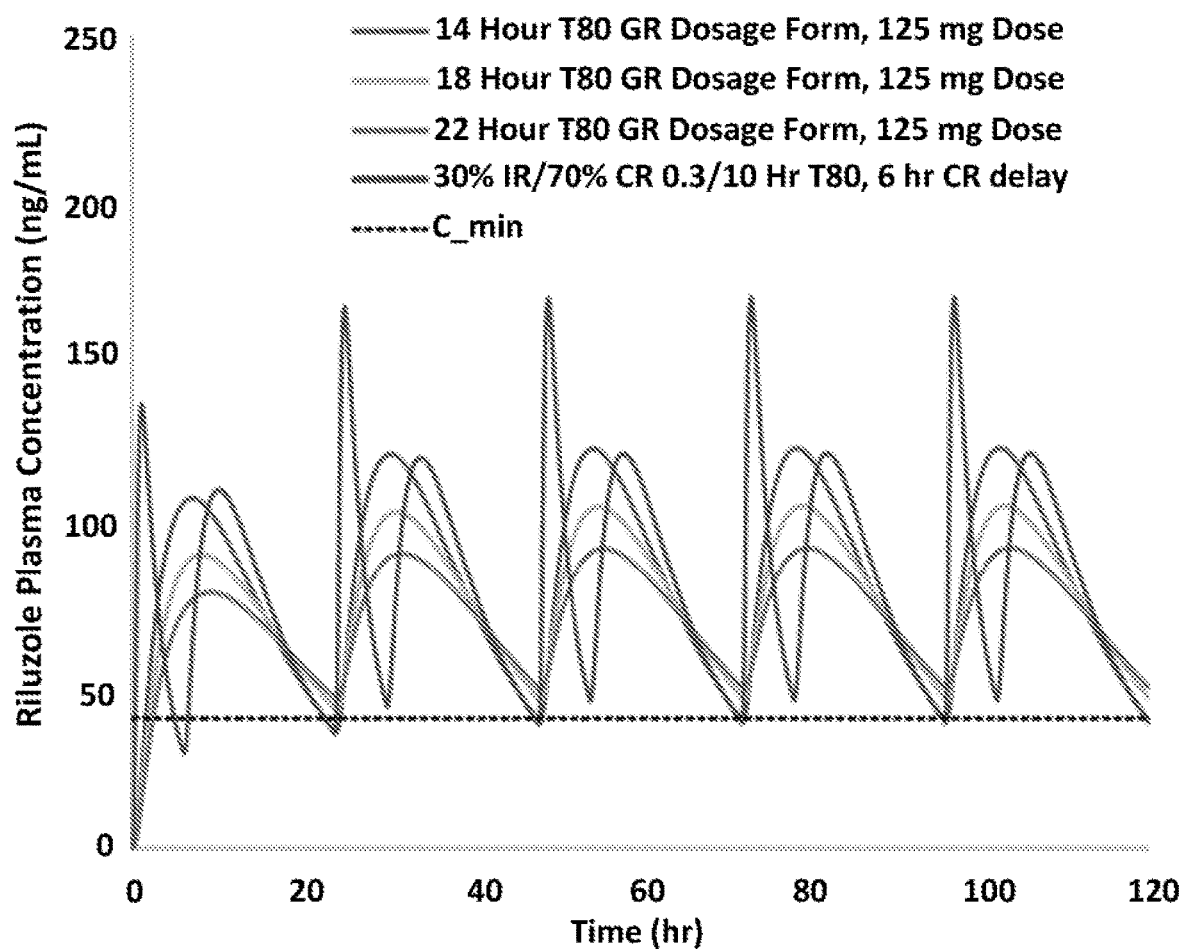
FIGS. 8A and 8B shows simulated blood plasma concentration vs. time plots (FIG. 8A) for a 125 mg dose of a gastroretentive form that remains in the stomach throughout the entire release profile, with theoretical release profiles used in each simulation shown in FIG. 8B.
Figure 8B:
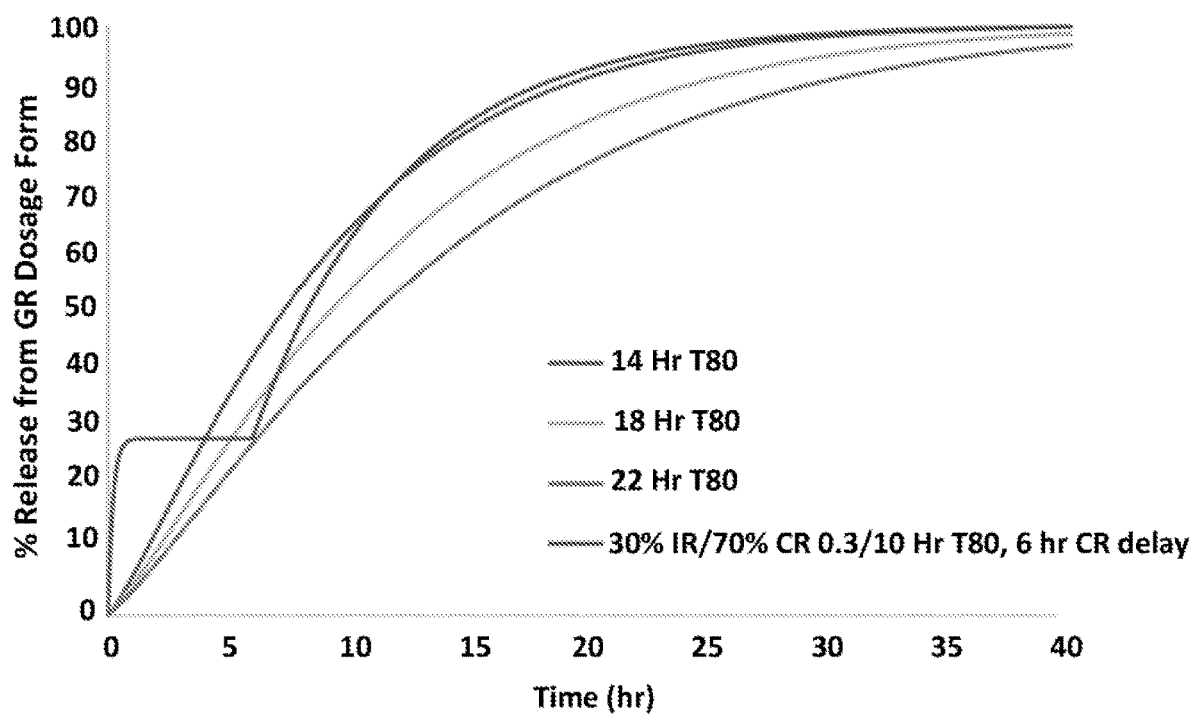

A gastroretentive formulation that remains in the stomach would achieve the target pharmacokientic profile. This is accomplished due to the retention of the dosage form in the stomach "maximizing" the absorption window of riluzole in the proximal small intestine. With this approach, the dosage form would not need to rely on any (or minimal) colonic absorption, reducing risk of incomplete absorption and deviating from the target profile. FIG. 8 and table 8 below show this concept in the riluzole absorption model as a function of release rate for both 100% modified release profiles or an exemplified 30/70 IR/MR combination profile.

Figure 10:
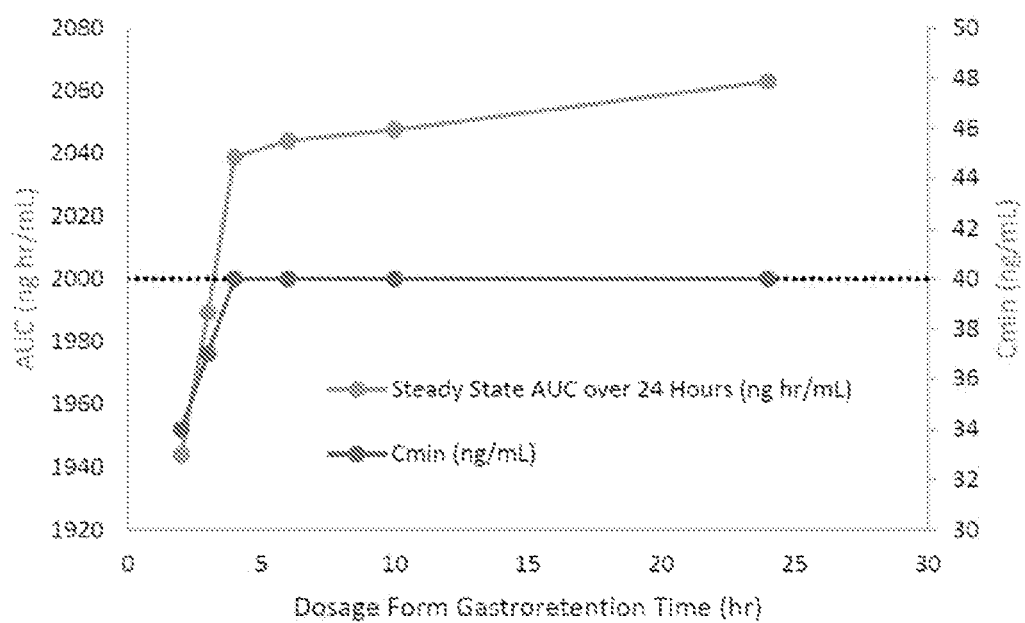
FIG. 10 shows simulated relationship between gastroretention time of the dosage form (hours) and the resulting impact on both steady state AUC over 24 hours (orange) as well as Cmin (blue) between dosing events.

FIG. 9 and Table 9 shows this concept simulating both fed and fasted state to predict the impact of a meal on drug release and absorption. Simulations suggest that the impact of food on blood plasma exposure could be potentially Minimum Gastrorentive Time for a Gastroretentive Formulation The following section determines the approximate minimum gastroretention time required to still achieve the TPP. Below in FIG. 10 is the simulated relationship between gastroretention time of the dosage form and the resulting impact on both steady state AUC over 24 hours (orange) as well as Cmin (blue) between dosing events. The simulations suggest that a minimum of approximately 4-6 hours of gastroretention can still achieve the TPP.

Multiparticulate Dosage Formulation (No Gastroretention)

Figure 12:
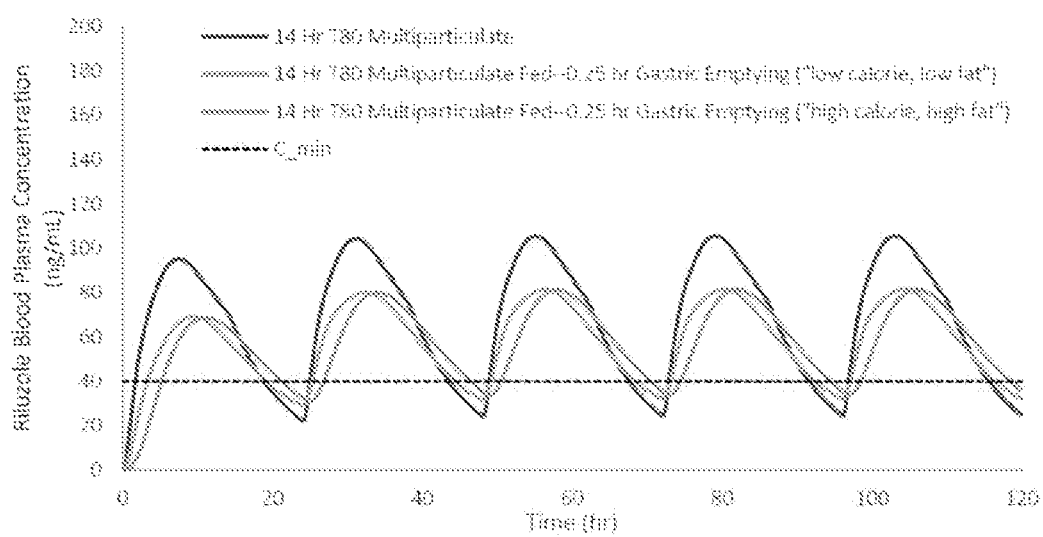
FIG. 12 shows simulated blood plasma concentration vs. time plots in the fasted and fed state (low and high calorie meals) for a 125 mg dose of a multiparticulate (no gastroretention) dosage form.

A multiparticulate dosage form (or other known delayed release formulations that do not release in the stomach) that releases over similar time profile to a gastroretentive dosage form, but does not retain in the stomach can achieve the TPP. A dosage form of this design disperses from a capsule or sachet into the GI tract and then releases drug as a function of the designed modified release profile. FIG. 12 and Table 11 below show this design in the riluzole absorption model as a function of release rate for both 100% modified release profiles or an exemplary 30/70 IR/DR combination profile (combination of immediate release portion and delayed release portion). The simulated profiles meet or come close to the minimum concentration target of 0.04 μg/mL. Based on this and additional simulations, a preferred IR fraction for an IR/MR combo for riluzole would be in the range of 10-50% (the remainder being the MR component), while a preferred MR delay time would be in the range of 4 to 8 hours and a preferred T80 for the MR component would be in the range of 6 to 14 hours.

Additional IR/MR simulated results obtained from the modeling are as follows:

| Dose (mg) | Release Description | % CR | AUC (24 hr, SS) | Cmax (ng/mL), SS | Cmin (ng/mL), SS | % Dose Absorbed |
|---|---|---|---|---|---|---|
| 125 | 10% IR/90% CR 0.3/10 Hr T80, 4 hr CR delay | 90 | 1634 | 118 | 25 | 76 |
| 125 | 10% IR/90% CR 0.3/10 Hr T80, 6 hr CR delay | 90 | 1491 | 108 | 28 | 70 |
| 125 | 10% IR/90% CR 0.3/10 Hr T80, 8 hr CR delay | 90 | 1340 | 97 | 17 | 63 |
| 125 | 20% IR/80% CR 0.3/10 Hr T80, 4 hr CR delay | 80 | 1696 | 112 | 24 | 79 |
| 125 | 20% IR/80% CR 0.3/10 Hr T80, 6 hr CR delay | 80 | 1567 | 114 | 26 | 73 |
| 125 | 20% IR/80% CR 0.3/10 Hr T80, 8 hr CR delay | 80 | 1434 | 116 | 23 | 67 |
| 125 | 30% IR/70% CR 0.3/10 Hr T80, 4 hr CR delay | 70 | 1758 | 156 | 22 | 82 |
| 125 | 30% IR/70% CR 0.3/10 Hr T80, 6 hr CR delay | 70 | 1644 | 157 | 24 | 77 |
| 125 | 30% IR/70% CR 0.3/10 Hr T80, 8 hr CR delay | 70 | 1526 | 159 | 26 | 71 |
| 125 | 40% IR/60% CR 0.3/10 Hr T80, 4 hr CR delay | 60 | 1817 | 198 | 21 | 85 |
| 125 | 40% IR/60% CR 0.3/10 Hr T80, 6 hr CR delay | 60 | 1719 | 199 | 22 | 80 |
| 125 | 40% IR/60% CR 0.3/10 Hr T80, 8 hr CR delay | 60 | 1617 | 200 | 24 | 75 |
| 125 | 50% IR/50% CR 0.3/10 Hr T80, 4 hr CR delay | 50 | 1876 | 239 | 19 | 88 |
| 125 | 50% IR/50% CR 0.3/10 Hr T80, 6 hr CR delay | 50 | 1792 | 240 | 21 | 84 |
| 125 | 50% IR/50% CR 0.3/10 Hr T80, 8 hr CR delay | 50 | 1706 | 241 | 22 | 80 |
| 125 | 30% IR/70% CR 0.3/6 Hr T80, 6 hr CR delay | 70 | 1774 | 156 | 22 | 83 |
| 125 | 30% IR/70% CR 0.3/10 Hr T80, 6 hr CR delay | 70 | 1644 | 157 | 24 | 77 |
| 125 | 30% IR/70% CR 0.3/14 Hr T80, 6 hr CR delay | 70 | 1533 | 158 | 25 | 71 |

TABLE 10

Tabulated data for simulations comparing plasma concentration vs. time plots (top) for a 125 mg dose of a multiparticulate (no gastroretention) dosage form. SS = steady state

| Dose (mg) | Release Description | % MR | AUC (24 hr, SS) | Cmax (ng/ml), SS | Cmin (ng/ml), SS | % Dose Absorbed |
|---|---|---|---|---|---|---|
| 125 | 14 Hr T80 | 100 | 1656 | 106 | 25 | 77 |
| 125 | 18 Hr T80 | 100 | 1497 | 90 | 26 | 70 |
| 125 | 22 Hr T80 | 100 | 1361 | 79 | 26 | 63 |
| 125 | 30% IR/70% MR 0.3/10 Hr T80, 6 hr MR delay | 70 | 1644 | 157 | 24 | 77 |

Figure 13:
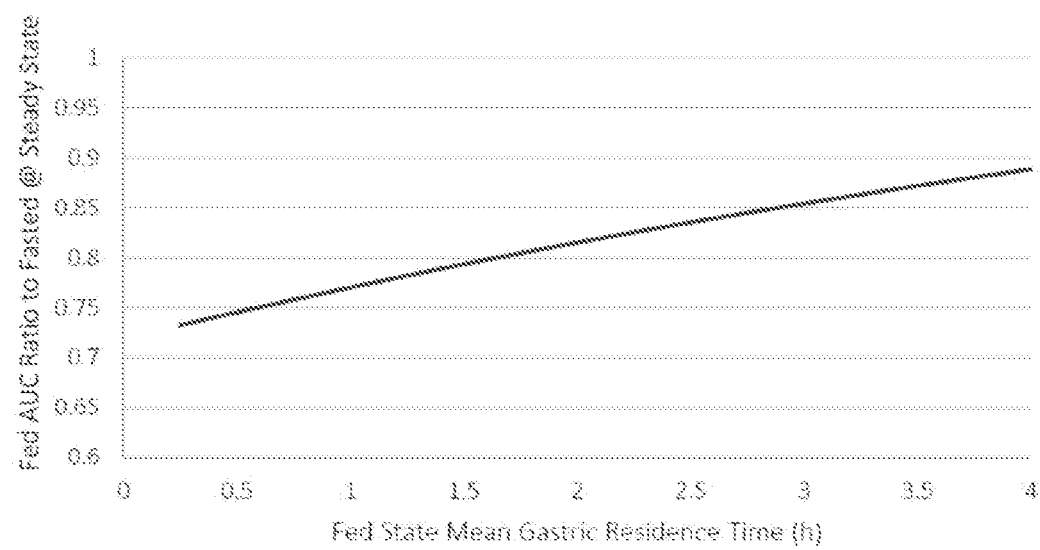
FIG. 13 shows parameter sensitivity of gastric emptying time in the fed state and resulting ratio of AUC to fasted state at steady state dosing (ratio of 1 means there is equal AUC in fed/fasted states).

FIG. 12 shows the multiparticulate formulation impact on prandial state, simulating both fed and fasted state to predict the impact of a meal on drug release and absorption. Simulations suggest that the impact of food on blood plasma exposure may be greater with a multiparticulate dosage form compared to a gastroretentive dosage form, but is still modest overall. A larger discrepancy occurs when gastric emptying is fast (low calorie meal) compared to slow (high calorie meal), as shown in FIG. 13 looking at the ratio of fed to fasted steady state AUC as a function of fed state gastric emptying time. The high calorie meal simulation is within 12% of the fasted state AUC at steady state, suggesting mitigation of a food effect is possible with extended gastric emptying. Extended gastric emptying is common in the fed state and is typically dictated by the amount of calories in the meal consumed. Accordingly, multiparticulate formulations may be further modified with known techniques to extend this window such as utilizing a buoyant capsule shell for the formulation or producing multiparticulates that float in GI fluid, delaying gastric emptying as a result.

Figure 14A:
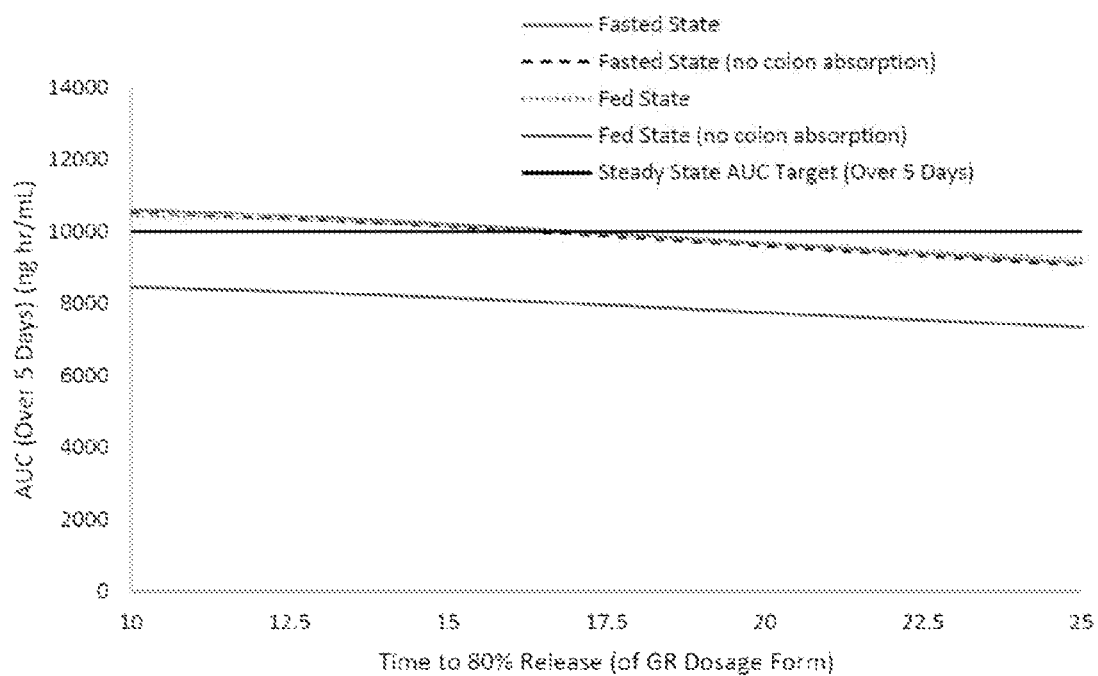
FIGS. 14A and 14B shows parameter sensitivity analysis (PSA) varying drug release rate—defined as "time to 80% release"—and measuring its impact on steady state AUC over a 5 day period for a gastroretentive dosage form (FIG. 14A) and a multiparticulate dosage form (FIG. 14B).
Figure 14B:
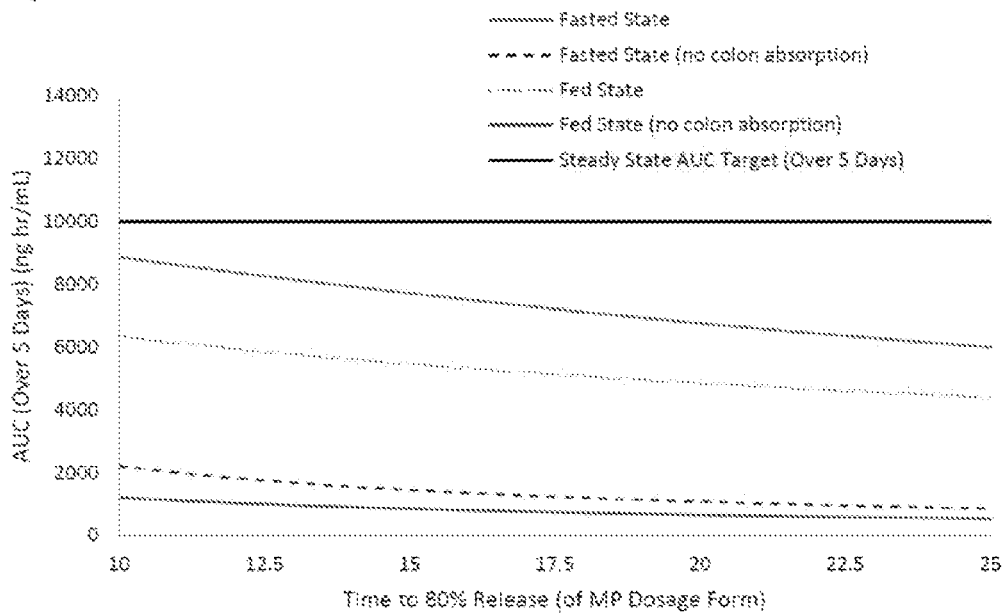

A parameter sensitivity analysis (PSA) was performed varying drug release rate across a range ("time to 80% release") and its impact on cumulative AUC over 5 days of dosing (AUC 0-5 days) for both a standard multiparticulate modified release dosage form (no gastroretention, relies extensively on colonic absorption and GI transit time) and a gastroretentive dosage form (does NOT rely heavily on colonic absorption or gastrointestinal transit time due to retention in stomach throughout release). As shown in FIG. 14, a PSA was performed for both fasted and fed state with both colonic absorption "turned on" and "turned off" to see the associated impacts on steady state AUC. The results of the PSA show the overall impact of release rate on steady state AUC for each dosage form type. The gastroretentive dosage form shows little to no impact on overall AUC. However, the multiparticulate dosage form (or any other dosage form that is not gastroretentive), shows a substantial impact on steady state AUC as a function of both drug release rate as well as across fed/fasted states when colonic absorption is "turned on" or "turned off".

Incorporating the amorphous form of riluzole into the modified release dosage form may optionally be utilized to provide a boost to solubilization capacity in the colon and overall improved absorption. One method to accomplish this is spray-drying an amorphous solid dispersion (ASD) of riluzole with a stabilizing dispersion polymer that provides sufficient chemical and physical stability for riluzole.

Another option is to adjust the loading dose higher to deliver more drug into systemic circulation to achieve the TPP. This would result in a partial "waste" of riluzole since incomplete absorption of a higher dose is likely, but the added drug mass may increase the total drug absorbed at the expense of this increase in unabsorbed riluzole (i.e. % dose absorbed drops with increasing dose, but total mass of riluzole increases due to more drug mass available for absorption during release and GI transit). The simulations suggest ample room to increase Cmax with a higher dose (currently far below 0.3 μg/mL upper limit), so this option may increase both steady state AUC and Cmin between dosing events in a conventional MR dosage form.

Reduced Liver Toxicity

The riluzole product monograph states that AUC increases 1.7 and 3 fold compared to healthy volunteers for patients with mild and moderate liver impairment, respectively. For geriatric populations, the monograph states that there are no observable differences in exposure in older patients. As such, it is of interest to explore the impact of a modified release dosage form on the blood plasma concentration profiles from these patient populations to identify potential benefits of a once daily "slower" absorption profile compared to the IR BID treatment currently marketed. Building on the absorption model framework established for the compartmental PK simulations above, a physiologically based pharmacokinetic (PBPK) model was developed to simulate blood plasma concentration profiles from a modified release dosage form architecture dosed once daily. A PBPK model affords the opportunity to look at different diseased states, race, gender and age and the resulting impact on drug disposition in the body. The PBPK model herein was based on differences in cytochrome 1A2 expression in patients with liver disease (for the liver impairment simulations, differences in cytochrome 1A2 expression were established using the GastroPlus PBPK model parameters, which has been established from large measured data sets across many compounds), as well as differences in tissue volumes and perfusion rates (for both liver impairment and geriatric simulations). For more details, please see the PBPK model parameter summary.

Figure 15A:
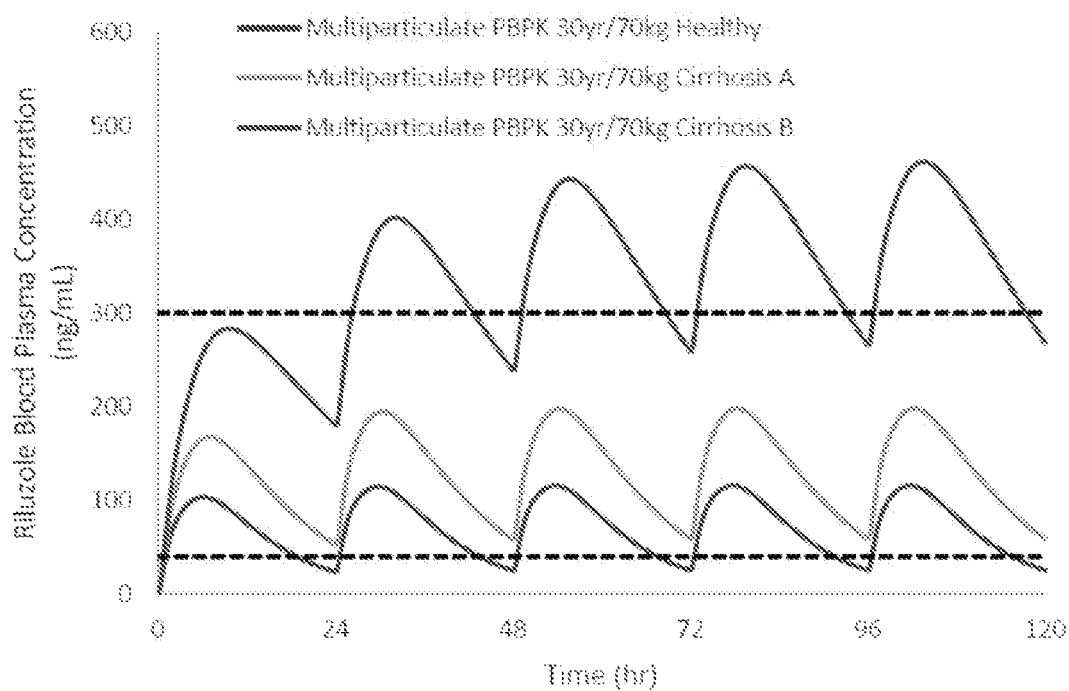
FIGS. 15A and 15B shows simulated blood plasma concentration profiles vs. time comparing 30 year old patients that are healthy or with cirrhosis level A and B (FIG. 15A) as well as a 70 year old healthy male to a 30 year old healthy male (FIG. 15B) using a GastroPlus PBPK model.
Figure 15B:
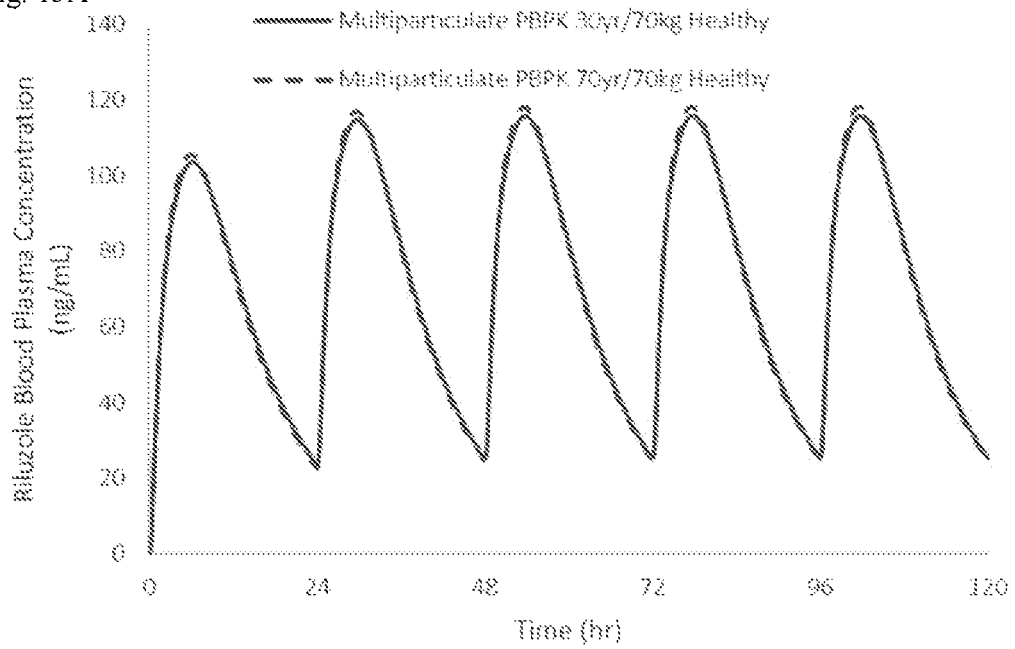
Figure 16:
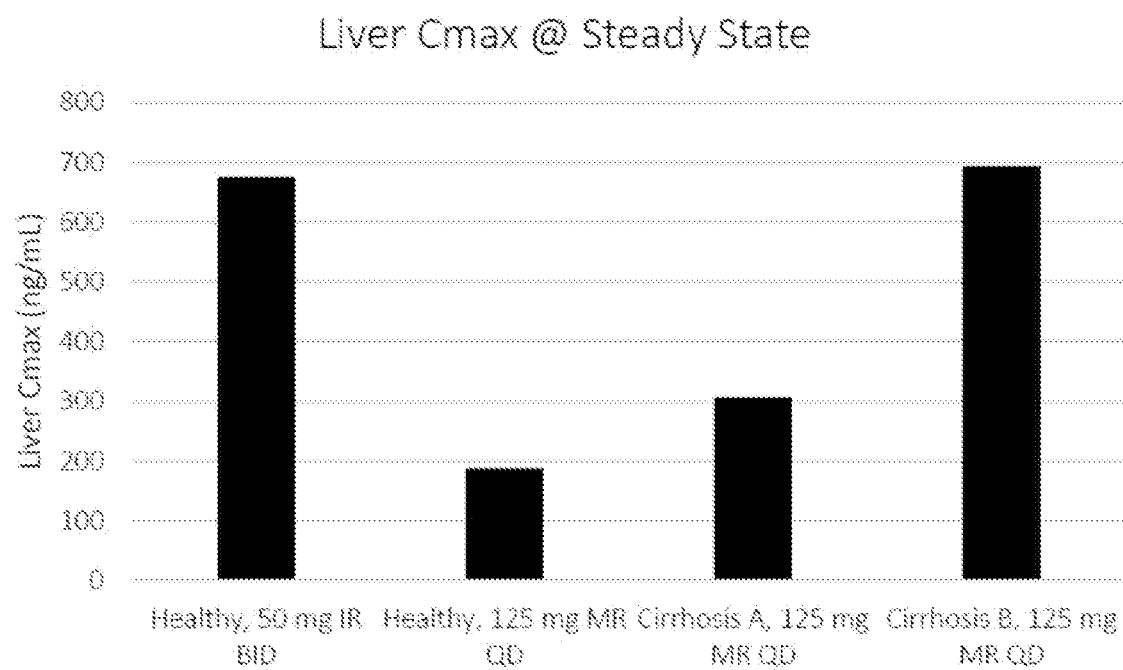
FIG. 16 shows simulated maximum liver concentrations from the PBPK model comparing the reference listed drug (RLD) treatment to a multiparticulate modified release dosage form treatment for healthy patients and those with liver impairment.

Simulations were performed using a multiparticulate dosage form architecture with a 14 hour T80 for a 30 year old male patient with cirrhosis level A and level B (mild and moderate), as well as a healthy 70 year old male subject (FIG. 15). Comparisons were made to a 30 year old healthy male subject. The simulations results suggest that if the TPP is maintained and liver toxicity is a result of maximum concentrations achieved in the liver (Cmax) rather than chronic exposure over time (AUC), then the modified release dosage formulation could benefit patients with some level of liver impairment compared to the current product on the market. In addition, FIG. 16 shows the simulated liver Cmax for each formulation treatment and conditions compared to the RLD product (50 mg IR BID), suggesting that a once daily MR dosage form could produce lower liver concentrations over time compared to the RLD treatment. The simulation comparing healthy males at age 30 and 70 also suggest no significant differences should be observed from these patients when considering differences in tissue volumes and blood flows, in agreement with reported data from the current product monograph.

Comparisons of Additional Controlled Release Formulations

Figure 17:
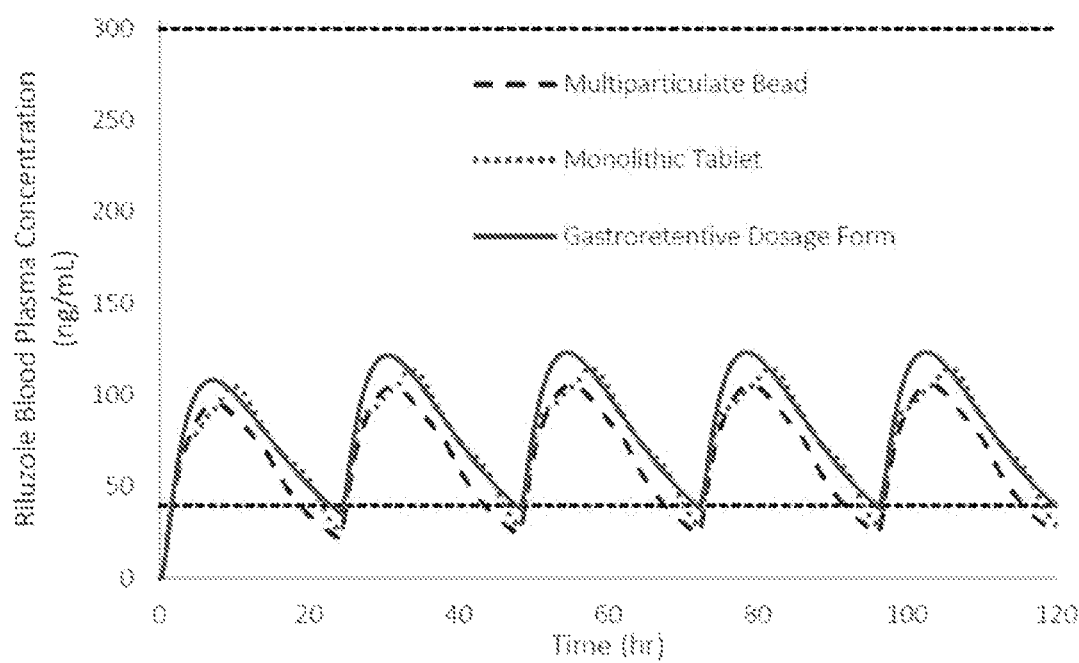
FIG. 17. Simulated blood plasma concentration profiles vs. time comparing a gastroretentive dosage form, a multiparticulate dosage form with no gastroretention, and a monolithic dosage form (osmotic push/pull or matrix) with no gastroretention.

FIG. 17 compares the simulated blood plasma concentration profiles and tabulated results for a gastroretentive dosage form, a multiparticulate dosage form with no gastroretention, and a monolithic dosage form (osmotic push/pull or matrix) with no gastroretention. All simulations use a 14 hr T80 release profile (100% modified release). The following controlled release formulation types can achieve the riluzole target product profile of T80 at 14-16 hrs: (1) gastroretentive formulation, (2) multiparticulate formulation, (3) matrix formulation, and (4) osmotic formulation.

Gastroretentive

Gastroretentive (GR) tablets are designed to be retained in the upper gastrointestinal tract for a prolonged period of time (typically 4-10 hours) to allow for extended drug release prior to emptying from the stomach. Gastric retention can be achieved by designing the dosage form to use one or more of the following mechanisms: flotation, expansion or swelling, increased density, and mucosal adhesion. Preferably, the floating and swelling mechanisms are utilized. Flotation can be achieved either using effervescent or non-effervescent systems. Effervescent systems rely on the chemical reaction of carbonates or bicarbonates with gastric fluid or with co-formulated acids (e.g. citric or tartaric acid) to generate a gas (e.g. carbon dioxide) that is subsequently entrapped in the polymer matrix and therefore reduces the apparent density of the dosage form, causing it to become buoyant. These systems can have a longer lag time prior to floating as the chemical reaction develops, which increases the risk of premature emptying from the stomach. Non-effervescent systems use a combination of swelling and gelling polymers that rapidly swell and trap air around the tablet core, which reduces the tablet density.

TABLE 11 outlines a general composition for a floating and swelling gastroretentive tablet using riluzole as the active ingredient.

| Example Materials | Function | Composition Range (%) |
|---|---|---|
| Riluzole | Active | 10-50 |
| Hydroxypropyl methylcellulose (HPMC) | Swelling | 5-50 |
| Hydroxyethylcellulose (HEC) | Polymer | |
| Hydroxypropylcellulose (HPC) | | |
| Polyethylene Oxide (PEO) | | |
| Sodium carboxymethyl cellulose | | |
| Crospovidone | Swelling | 0-10 |
| Croscarmellose sodium | Polymer Aid | |
| Microcrystalline cellulose | | |
| Mannitol | | |
| Sodium bicarbonate | Gas-generating Agent | 0-10 |
| Acids (e.g. citric acid, tartaric acid) | | |
| Silicon dioxide | Glidant | 0-2 |
| Magnesium stearate | Lubricant | 0.5-2 |
| Sodium stearyl fumarate | | |

Multiparticulate

Multiparticulates consist of multiple discrete drug-containing particles that are packaged together to make up a single unit dose. Some advantages of multiparticulates include easy modification to meet a range of target dissolution profiles, improved swallowability, high dose flexibility and accuracy of administered dose, and suitability for a range of dosage forms (e.g. capsules and tablets). Multiparticulates particles are typically spherical and approximately 0.1-3 millimeters in diameter. Four main types of multiparticulates are lipid multiparticulates (LMPs), spray-layered multiparticulates, pellets, and mini tablets. Each type of multiparticulate can be designed as immediate release, controlled release, or a combination of the two.

LMPs may comprise a hydrophobic and low permeability lipid as main matrix, water soluble pore former, and the drug in either crystalline or amorphous form. LMPs are produced by melting all components together (unless crystalline API is desired, then it is a suspension) into a uniform mixture followed by particle generation using melt-spray congeal (MSC) processing. Drug release from this technology relies on water permeation into the particle, dissolution of the pore former and drug within the particle, and ultimate diffusion of the drug-containing solution from the particle. The matrix selection, active loading, and amount of pore former in the formulation are key handles in fine tuning the drug release to achieve any TPP. An additional controlled release coating could optionally be applied to the exterior of the LMP particles. A 30/70 IR/CR LMP dosage form is preferably used for riluzole and can be produced by either coating a controlled release LMP core with an IR coating containing riluzole or co-dosing two separate LMP cores—one IR and one CR, into a single dosage form product (e.g. capsule). Table 12 outlines an example composition for a riluzole-containing LMP.

TABLE 12

Example composition for lipid multiparticulate (LMP) core formulation for riluzole.

| Example Materials | Function | Composition Range (%) |
|---|---|---|
| Riluzole | Active | 10-60 |
| Stearyl alcohol (StOH) | Lipid Matrix | 30-90 |
| Glyceryl tristearate (GTS) | | |
| Carnuba Wax | | |
| Glyceryl dibehenate | | |
| Poloxamer 407 | Pore Former | 0-20 |
| Gelucire | | |

Spray-layered mulitparticulates are manufactured by layering drug onto either a sucrose or microcrystalline cellulose core using a fluid bed coater. To achieve the riluzole TPP, this would entail two separate coatings—one 'immediate release' portion containing the drug and a second outer controlled release coating that limits water permeation. The IR portion may comprise a combination of drug and polymer binder that is sprayed out of an appropriate solvent or antisolvent if a layer of crystalline drug is desired. This layer can have either a high or low drug loading depending on the target unit dose and final dosage form fill weight. The controlled release portion may comprise an enteric material that delays release of the drug layer until a certain pH is reached. A 30/70 IR/CR Spray-layered multiparticulate dosage form could be achieved by adding an outer drug coating layer (i.e. 3 coatings total). Table 10 outlines a general composition for a riluzole containing spray-layered multiparticulate.

TABLE 13

Example composition for spray-layered multiparticulate formulation for riluzole.

| Example Materials | Function | Composition Range per Layer (%) |
|---|---|---|
| Suglet (sugar sphere) | Compressible Core | NA |
| Microcrystalline cellulose | | |
| Drug Coating Layer | | |
| Riluzole | Active | 10-90 |
| Hydroxypropyl methylcellulose (HPMC) | Binder | 10-90 |
| Hydroxypropylcellulose (HPC) | | |
| Hydroxypropyl methylcellulose acetate succinate (HPMCAS) | | |
| Eudragit L | | |
| Controlled Release Coating Layer | | |
| Eudragit RS/RL | Film-forming polymer | 70-100 |
| Ethyl Cellulose | | |
| Cellulose Acetate | | |
| Polyethylene glycol | Permeability enhancer | 0-20 |
| Delayed Release Coating Layer | | |
| Hydroxypropyl methylcellulose acetate succinate (HPMCAS) | Film-forming polymer | 70-100 |
| Eudragit L and/or Eudragit S | | |

Matrix Formulation

Matrix formulations are monolithic dosage forms that combine the drug in crystalline or amorphous form with rate-controlling material(s), which may be polymers, and other inactive ingredients. Some benefits of matrix tablets are that they have a relatively simple formulation, use a conventional tablet manufacture process that is readily scalable, and can accommodate both low and high drug loads. Optionally, a matrix formulation contains hydrophilic and/or hydrophobic polymers that hydrate and rapidly swell, forming a gel layer around the tablet core. Drug release occurs by diffusion through the gel layer and/or erosion of the tablet, and the ratio of the various components can be adjusted to achieve the TPP. The use of pH-triggered polymers can also contribute to the release profile as the tablet travels through the GI tract. Table 14 outlines an example matrix tablet composition using riluzole as the active ingredient.

TABLE 14

Example composition for matrix monolith tablet formulation for riluzole.

| Example Materials[21] | Function | Composition Range (%) |
|---|---|---|
| Tablet Core | | |
| Riluzole | Active | 10-60 |
| Hydroxypropyl methylcellulose (HPMC) | Controlled Release Component | 10-60 |
| Hydroxyethylcellulose (HEC) | | |
| Hydroxypropylcellulose (HPC) | | |
| Hydroxypropyl methylcellulose acetate succinate (HPMCAS) | | |
| Polyethylene Oxide (PEO) | | |
| Polyacrylic acid | | |
| Lactose | Filler | 0-30 |
| Microcrystalline cellulose | | |
| Polyvinylpyrrolidone (PVP) | | |
| Polyvinylpyrrolidone vinyl acetate (PVPVA) | | |
| Silicon dioxide | Glidant | 0.5-2 |
| Magnesium stearate | Lubricant | 0.5-2 |
| Sodium stearyl fumarate | | |
| Coating (Optional) | | |
| Hydroxypropyl methylcellulose (HPMC) | Controlled Release Component | 0-100 |

Osmotic Formulation

Osmotic controlled release delivery systems may comprise a core that is coated in a semi-permeable membrane that controls water ingress into the core as the means to control drug release. In some embodiments, the tablet core contains an osmotic agent and a water-swellable polymer that expands in volume as the core absorbs water. The coating is designed to have one or multiple delivery ports where the drug solution or suspension is extruded out of the formulation over a time frame of 8-24 hours using zero-order kinetics. Osmotic formulations release drug at a rate that is independent of pH, ionic strength, fasted/fed states, and hydrodynamics around the tablet.

Swellable Core Technology (SCT)

SCT formulations can accommodate both crystalline and amorphous drug loadings. This dosage form comprises a bilayer tablet core where one layer contains the drug substance and the other layer acts as the swelling agent. Both layers contain the same entraining polymer (preferably polyethylene oxide) but at different molecular weights to allow for fine-tuning of the viscosity differences between the two layers to maximize total extent of release. The bilayer core is then coated in a semi-permeable, insoluble membrane containing a film-forming polymer and a pore-forming polymer. Table 16 outlines a general SCT tablet composition using riluzole as the active ingredient.

TABLE 15

Example composition for swellable-core technology (SCT) controlled release tablet formulation for riluzole.

| Materials | Function | Composition Range per Layer/ Coating (%) |
|---|---|---|
| Drug Layer | | |
| Riluzole | Active | 2-50 |
| Polyethylene Oxide (PEO) | Entraining Polymer | 70-90 |
| Hydroxypropyl cellulose (HPC) | Binder (as needed) | 0-10 |
| Hydroxypropyl methylcellulose (HPMC) | | |
| Salt (e.g. sodium chloride) | Osmogen | 0-10 |
| Sugar (e.g. Mannitol, xylitol) | | |
| Silicon dioxide | Glidant | 0-2 |
| Magnesium stearate | Lubricant | 0.5-1 |
| Sodium stearyl fumarate | | |
| Sweller Layer | | |
| Polyethylene Oxide (PEO) | Entraining Polymer | 60-80 |
| Salt (e.g. sodium chloride) | Osmogen | 5-40 |
| Iron Oxide Blue Lakes No. 2 | Colorant | 0.2-0.5 |
| Magnesium stearate | Lubricant | 0.5-1 |
| Sodium stearyl fumarate | | |
| Semi-Permeable Coating | | |
| Cellulose acetate | Film-forming polymer | 70-95 |
| Polyethylene Glycol | Permeability enhancer | 5-30 |

Asymmetric Membrane Technology (AMT)

Another type of osmotic pump is an asymmetric membrane technology (AMT) formulation. AMT formulations can also accommodate crystalline or amorphous water soluble drug loadings. AMT formulations comprise a single layer tablet core that is coated with a porous, semipermeable coating with a similar composition as for SCT tablets, which controls drug release from the tablet. The water permeability (i.e. porosity) of the coating and the osmotic pressure within the tablet dictate the drug release rate. As water enters the tablet, the hydrostatic pressure increases, forcing the drug out through the coating pores and therefore it doesn't require the need for laser drilled orifice(s) as a separate procedure. Table 13 outlines a general AMT tablet composition using riluzole as the active ingredient.

TABLE 16

Example composition for asymmetric membrane technology (AMT) tablet formulation for riluzole.

| Materials | Function | Composition Range per Layer/ Coating (%) |
|---|---|---|
| Tablet Core | | |
| Riluzole | Active | 10-50 |
| Polyethylene glycol | Solubilizer | 10-50 |
| Polypropylene glycol | | |
| Sodium lauryl sulfate | | |
| Cyclodextrins | | |
| EDTA | | |
| Trisodium phosphate | | |
| Microcrystalline cellulose | Binder | 15-25 |
| Lactose | | |
| Salt (e.g. sodium chloride, potassium phosphate) | Osmogen | 0-60 |
| Sugar (e.g. mannitol, sorbitol, xylitol) | | |
| Magnesium stearate | Lubricant | 0.5-2.5 |
| Sodium stearyl fumarate | | |
| Semi-Permeable Coating | | |
| Cellulose acetate | Film-forming polymer | 70-95 |
| Polyethylene Glycol | Permeability enhancer | 5-30 |

Additional Formulation Variations

Minitablet versions of the afore-mentioned formulations may optionally be used. Minitablets can have cores of similar compositions to the matrix tablets or AMT tablets, and various types of known coatings can be applied by pan coating or fluid bed coating depending on the tablet size and density. Their rates of release are expected to be intermediate to larger tablets (monoliths) and MPs, with the added flexibility of coatings to augment their ability to meet the TPP.

Basis for GastroPlus v 9.7 (Simulations Plus, Inc.) Simulated Model

A multicompartment model was used to fit to the observed plasma concentration vs. time intravenous data published by Le Liboux et al. to establish PK terms, followed by evaluating the model's accuracy against observed oral data from two separate studies found in the literature (Le Liboux et al. cited above and Abbara C et al., *Br J Clin Pharmacol.*, 2011; 71(3):403-410).

TABLE A1

Reference In vivo data details from Le Liboux et al. and Abbara C. et al. studies

| Description | Le Liboux et al. Study | Abbara C. et al. |
|---|---|---|
| Species | Human | Human |
| Dose (mg) | 100 mg QD and BID (oral), 50 mg QD (IV) | 50 mg over 5 days |
| Fed/Fasted | Both | Fasted |
| Average Subject Weight (kg) | 70 | 29 |

TABLE A2

Treatment details for reference in vivo data

| Description | Fed/Fasted | Route | Source | Architecture |
|---|---|---|---|---|
| 100 mg Riluzole QD | Fasted | Oral | Le Liboux et al. J Clin. Pharmacol 1997; 37: 820-827 | Tablet |
| 100 Riluzole QD | Fed | Oral | | Tablet |
| 100 mg Riluzole BID | Fasted | Oral | | Tablet |
| 100 mg Riluzole QD | Fasted | IV | | Solution |
| 50 mg Riluzole QD Over 5 Days | Fasted | Oral | Abbara C, Estournet B, Lacomblez L, et al. Br J Clin Pharmacol. 2011; 71(3): 403-410. | Tablet |

TABLE A3

Drug physicochemical properties used in the absorption model

| Property | Value | Source | Commentary |
|---|---|---|---|
| Molecular Weight (g/mol) | 234.2 g/mol | ADMET calc | — |
| pKa | 3.8 | Rilutek ® product monograph | This is the reported basic pKa. As such, riluzole has increased solubility in the low pH environment of the stomach compared to the small intestine. |
| LogD @ pH 6.5 | 2.4 @ pH 6.5 | ADMET calc | Calculated LogD plays a role in determining what the absorption scale factor (ASF) (in units of $cm^{-1}$) is in each compartment in the GastroPlus ACAT model. For reference, your absorption rate constant, Ka ($s^{-1}$), is Peff (cm/s) × ASF ($cm^{-1}$). As ASF increases, so does Ka. |
| Effective Permeability ($\times 10^{-4}$ cm/s) | $3 \times 10^{-4}$ cm/s (fasted state) $0.88 \times 10^{-4}$ cm/s (fed state, high fat/high calorie) $1.25 \times 10^{-4}$ cm/s (fed state, low fat/low calorie) | ADMET calc (fasted) Derived by accounting for added bile/fat relative to fasted state (fed) Riluzole aqueous suspensions. European Patent EP 2405890 B1. Nov. 28 2012. | This is a calculated value that is driven by characteristics such as molecular weight, charge state and lipophilicity of the drug. See food effect and permeability rationale for more information on proposed fed/fasted permeability differences. any bile salt micelles or other solubilizing agents. |
| Biorelevant Solubilities (mg/mL) | 0.377, pH 6, 2.8 mM SIF 0.917, pH 5.4, 22 mM SIF | Calculated in GastroPlus v9.7 | These calculated values define the total solubilized drug concentrations in the absorption model, accounting for bile salt micelles in GI fluid using LogP as the basis for the calculation. |
| Particle density (g/cm3) | 1.2 | ADMET | Standard assumed true density for a solid particle. |
| Diffusion Coefficient ($\times 10^{-5}$ cm2/s) | 1.05 | ADMET | Calculated from drug molecular weight at infinite dilution. |

Permeability reduction accounts for the increased bile salt micelle concentrations in the fed state—which impacts the amount of drug that partitions into the bile salt micelles through the micelle partition coefficient—and assumes the drug partitions into the fat from the meal at a 1:1 ratio. The end result after accounting for these changes in the fed state results in a reduction of the permeability from $3\times10^{-4}$ cm/s to $0.88\times10^{-4}$ cm/s for a high fat/high calorie meal simulation and to $1.25\times10^{-4}$ cm/s for a low fat/low calorie meal simulation. This method of permeability reduction results in very good prediction accuracy from the model against observed data in fed subjects.

For the immediate release simulations (this includes the fed/fasted simulations against Le Liboux et al. and Abbara C. et al. observed data as well as the MAD simulations), a standard Johnson model was used to simulate dissolution. The Johnson model is an adaptation of classical Noyes-Whitney dissolution theory, where dissolution rate is driven by solubility and effective surface area of drug particles.

TABLE A4

Immediate release dissolution model description for the riluzole absorption model

| Parameter | Riluzole Fasted | Riluzole Fed | Commentary |
|---|---|---|---|
| Dissolution Model | Johnson | Johnson | Johnson: This is an adaptation of Noyes-Whitney dissolution theory, where dissolution is controlled by a concentration gradient and effective surface area defined by particle size. |
| Reference Temperature (° C.) | 37 | 37 | n/a |
| Bile Salt Effect "Biorelevant Solubilities" (mg/mL) | 0.377, pH 6, 2.8 mM SIF 0.917, pH 5.4, 22 mM SIF | 0.377, pH 6, 2.8 mM SIF 0.917, pH 5.4, 22 mM SIF | This calculated value accounts for the impact of bile salt micelles on dissolution rate by adjusting the concentration gradient arising from the increased apparent solubility as well as adjusting drug diffusivity to account for the impact of bile salts on the drug diffusing from the particle surface. |
| Diffusion Layer Thickness (μm) | Changes with particle radius <30 | Changes with particle radius <30 | Given the particle diameter is set to 10 μm, the assumed diffusion thickness from the particle surface is set to the particle diameter. This is the thickness of the diffusion controlled region between the drug solid particle surface and bulk fluid. |
| Mean Particle Radius (μm) | 5 | 5 | An assumed value based on the rapid absorption observed from IR formulations (short Tmax). |

For all modified release simulations except the IR/MR combo profile, the Weibull function was used within GastroPlus to simulate each theoretical profile. This is a function that is designed to accommodate all types of modified release profiles by fitting the data to a statistical function. Each parameter within this function is described below in terms of what it means and its significance. For the IR/MR combo simulation, the theoretical profile was calculated outside GastroPlus due to additional caclulations required for such a release profile.

Pharmacokinetics for riluzole were established from intravenous data reported by Liboux et al. These data were a 30 minute intravenous infusion of 50 mg riluzole. The IV data was then fit to a compartmental model where the best fit was observed for three compartments—one central compartment plus two peripheral compartments. Physiologically, this means that the drug distributes out of systemic circulationon a similar time scale to the rate at which it eliminates via hepatic and renal pathways. It should be noted that Le Liboux reports that single dose pharmacokinetics

TABLE A5

Modified release dissolution model description for the riluzole absorption model

| Parameter | All modified release drug records except the IR/MR combo | IR/MR combo[38] | Commentary |
|---|---|---|---|
| Time lag (hr) | 0 | 0 for IR, 6 hr MR | Allows a user to define an amount of time where no drug release occurs in vivo. |
| Max released (%) | 100 | 100 | How much of the drug release from the MR dosage form |
| F (fraction) | 1 | 1 | This is how much of the profile is a single, double, or triple Weibull function. This model used a single Weibull so the fraction is 1. |
| A (time scale) (hrs[b]) | Ranges from 15-25 | Not used for IR/MR | Defines your x axis time scale. A larger value increases release time. |
| Time to 80% drug release (T80) | Ranges from 14-22 hours | 0.3 hr for IR, 10 hr for MR | Equivalent to parameter A above, but expressed simply in terms of time rather than a statistical parameter. |
| b (shape) | 1.2 | Not used for IR/MR | Defines the shape of the MR release curve. A value of 1 follows a first order exponential relationship $(1 - e^{-kt})$ | were not sufficient in describing multiple dose data, claiming a change in biotransformation as the likely cause. Therefore, the riluzole clearance value was adjusted for multiple dose simulations by decreasing the clearance by 20% compared to the single dose clearance. The metric for the reduction in clearance was established by adjusting clearance to match the Cmin values reported by Le Liboux et al. in their 100 mg BID treatment arm (~0.04 μg/mL) to the Cmin from the present model's 100 mg BID simulation. This resulted in roughly a 20% clearance reduction. All other PK parameters were held constant at the fitted values from single dose IV data. This adjusted clearance was evaluated against observed data from an independent multiple dosing study published by Abbara C. et al. and provided good prediction of the data.

larly an issue for patients with mild to severe liver impairment. The riluzole product monograph states that AUC increases 1.7 and 3 fold compared to healthy volunteers for patients with mild and moderate liver impairment, respectively. For geriatric populations, the monograph states that there are no observable differences in exposure in older patients. As such, the PBPK model should be able to predict to a reasonable degree the exposure increases for patients with liver impairment as well as the lack of differences expected in geriatric populations compared to healthy middle-aged subjects (as the baseline). The method used to scale from healthy individuals to patients with liver disease (Cirrhosis level A and B) of older age (70 yr) was the default PBPK model in Gastroplus, accounting for differences in blood flow, tissue volume as well as enzyme expression. The

TABLE A6

Pharmacokinetic parameters used in the riluzole absorption model

| Parameter | Value | Source | Commentary |
|---|---|---|---|
| Body weight (kg) | 70 | assumed | Standard BM assumption for healthy volunteer |
| First Pass Extraction (%) | 40 | Assumed value based on bioavailability of 60% from current RLD. Complete absorption is assumed here. Calculated values considering clearance relative to liver blood flow closely agrees with this value | Typically estimated from liver blood flow and liver clearance in GastroPlus v9.7. This is calculated as CL/blood to plasma ratio/liver blood flow. For riluzole, this calculates to ~42%, closely matching assumed value of 40% based on reported bioavailability. |
| Fraction of drug unbound in plasma (%) | 11.8 | Estimated from LogP in GastroPlus | Fraction of drug freely dissolved in plasma as opposed to drug bound to proteins and fats in plasma. |
| Blood/plasma concentration ratio. | 1.19 | Estimated in GastroPlus | This value is used to convert ratio of drug in plasma to whole blood for calculating first pass liver extraction. |
| Clearance (L/h/kg) | 0.64 (single dose) 0.50 (multiple dose) | IV data fit in PKPlus | PK Plus is GastroPlus uses a compartmental fit model to provide a best fit to the observed IV data as a function of dose, infusion time and subject weight. In this case, the best fit was obtained from a three compartment model with a clear initial distribution phase followed by an elimination phase and likely slow redistribution phase. |
| Volume of distribution (central compartment) (L/kg) | 0.386 | IV data fit in PKPlus | |
| Elimination half-life (h) | 7.1 (single dose) 7.9 (multiple dose) | IV data fit in PKPlus | |
| K12 (1/h) | 4.56 | IV data fit in PKPlus | |
| K21 (1/h) | 1.9 | IV data fit in PKPlus | |
| Volume of distribution (2nd compartment) (L/kg) | 0.93 | IV data fit in PKPlus | |
| K13 (1/h) | 0.56 | IV data fit in PKPlus | |
| K31 (1/h) | 0.14 | IV data fit in PKPlus | |
| Volume of distribution (3rd compartment) (L/kg) | 1.55 | IV data fit in PKPlus | |

A physiological-based pharmacokinetic (PBPK) model was established using the same framework for the general model described herein, but differs in the pharmacokinetic treatment of riluzole after the drug gets absorbed. PBPK models allow a user to simulate drug disposition throughout all tissues in the body as a function of time and affords the opportunity to look at simulated exposure across diseased states, age, ethnicity, among others. Riluzole demonstrates liver toxicity issues for some subjects across many patient populations—even healthy individuals—but it is particumeasured clearance of riluzole was taken from healthy volunteers (Le Liboux et al. study) as a baseline (used clearance value adjusted for multiple dosing) for the liver clearance in a 30 yr/70 kg healthy adult. Liver clearance of riluzole was adjusted in proportion to the differences in CYP 1A2 expression—the main enzyme responsible for riluzole metabolism in the liver—across each patient population. The output is a unique physiology for each simulated scenario (liver disease and age) that accounts for blood flow, tissue volume and metabolism differences. Table A7 shows the parameters considered when scaling riluzole clearance for each simulated population. For reference, a comparison was made to the traditional compartmental model using the 100 mg fasted data from the Le Liboux et al. study and found both the PBPK and compartmental models agree well with each other, showing accuracy in making simulations for specific patient populations using the PBPK strategy.

TABLE A7

Tabulated parameters for scaling clearance as a function of CYP 1A2 expression across different populations. In addition to accounting for metabolism, tissue blow flow and volumes were also used and originate from the default PBPK model used in GastroPlus.

| Population (males)[46] | CYP 1A2 Expression (mg enzyme/ gram tissue) | Gastro PBPK Adjusted Clearance Based on Tissue Volume and Perfusion Rate (L/hr) | CYP 1A2 Ratio to healthy subjects | Adjusted Liver Clearance for simulation (L/hr) |
|---|---|---|---|---|
| 30 yr/70 kg healthy | 1.15E−01 | 34.8 | — | 34.8 |
| 30 yr/70 kg Cirrhosis Class A | 7.30E−02 | 37.1 | 0.64 | 23.5 |
| 30 yr/70 kg Cirrhosis Class B | 3.00E−02 | 36.0 | 0.26 | 9.4 |
| 70 yr/70 kg healthy | 1.15E−01 | 32.5 | 1.0 | 32.5 |

With the riluzole absorption model framework established, model accuracy against observed oral data for riluzole was determined. Simulations were measured against observed data reported by Le Liboux et al. for riluzole dosed at 100 mg in both the fed and fasted states and Abbara C. et al for riluzole dosed at 50 mg over 5 days in the fasted state (data collected on day 5). Observed data was digitized for the purposes of overlaying on the same plot as each simulation. For fed state simulations, the data agrees better when colonic absorption is "turned off", indicating that the model predicts some risk for dosage forms that require extensive colonic absorption. For all simulations, model accuracy was reliable across both observed data sets.

What is claimed is:

1. A pharmaceutical composition comprising from about 75 mg up to about 300 mg of a compound selected from the group consisting of: N-methyl-2-(methylamino) -N-(2-oxo-2-((6-(trifluoromethoxy)benzo[d]thiazol-2-yl)amino)ethyl) acetamide, 2-(ethylamino)-N-methyl-N-(2-oxo-2-((6-(trifluoromethoxy)benzo[d]thiazol-2-yl)amino)ethyl) acetamide, 2-(isopropylamino)-N-methyl-N-(2-oxo-2-((6-(trifluoromethoxy)benzo[d]thiazol-2-yl)amino)ethyl) acetamide, and 2-(tert-butylamino) -N-methyl-N-(2-oxo-2-((6-(trifluoromethoxy)benzo[d]thiazol-2-yl)amino)ethyl) acetamide, wherein the pharmaceutical composition provides a Cmax at steady state of less than about 0.3 mcg/mL for at least about 24 hours.

2. The pharmaceutical composition of claim 1, wherein the pharmaceutical composition provides a Cmin at steady state of at least about 0.04 mcg/mL for at least about 24 hours.

3. The pharmaceutical composition of claim 2, wherein the pharmaceutical composition provides an AUC at steady state of from about 1.5 mcg*h/mL to about 4 mcg*h/mL for at least about 24 hours.

4. The pharmaceutical composition of claim 3, wherein the AUC at steady state is about 2.5 mcg*h/mL for at least about 24 hours.

5. The pharmaceutical composition of claim 1, wherein the pharmaceutical composition is formulated to be administered once a day.

6. The pharmaceutical composition of claim 2, wherein the pharmaceutical composition is formulated to be administered once a day.

7. The pharmaceutical composition of claim 3, wherein the pharmaceutical composition is formulated to be administered once a day.

8. The pharmaceutical composition of claim 1, wherein the pharmaceutical composition is formulated to be taken without food.

9. The pharmaceutical composition of claim 3, wherein the pharmaceutical composition is formulated to be taken without food.

10. The pharmaceutical composition of claim 1, wherein the pharmaceutical composition is formulated to reduce liver toxicity compared to 50 mg of an immediate release form of riluzole given twice a day.

11. The pharmaceutical composition of claim 3, wherein the pharmaceutical composition is formulated to reduce liver toxicity compared to 50 mg of an immediate release form of riluzole given twice a day.

12. A method of treating Alzheimer's disease, amyotrophic lateral sclerosis, obsessive compulsive disorder, or spinocerebellar ataxia comprising administering to a subject in need thereof a composition of claim 1.

13. A method of treating Alzheimer's disease, amyotrophic lateral sclerosis, obsessive compulsive disorder, or spinocerebellar ataxia comprising administering to a subject in need thereof a composition of claim 3.

14. A method of treating Alzheimer's disease, amyotrophic lateral sclerosis, obsessive compulsive disorder, or spinocerebellar ataxia comprising administering to a subject in need thereof a composition of claim 5.

15. A method of treating Alzheimer's disease, amyotrophic lateral sclerosis, obsessive compulsive disorder, or spinocerebellar ataxia comprising administering to a subject in need thereof a composition of claim 7.

16. The method of claim 15, wherein the subject is suffering from Alzheimer's disease.

17. The method of claim 15, wherein the subject is suffering from amyotrophic lateral sclerosis.

18. The method of claim 15, wherein the subject is suffering from obsessive compulsive disorder.

19. The method of claim 15, wherein the subject is suffering from spinocerebellar ataxia.

* * * * *